(12) United States Patent
Yifat et al.

(10) Patent No.: US 11,621,096 B2
(45) Date of Patent: *Apr. 4, 2023

(54) RADIATION PROTECTION APPARATUS AND MATERIALS THEREFOR

(71) Applicant: Radiaction Ltd., Tel Aviv (IL)

(72) Inventors: Jonathan Yifat, Ramat Hasharon (IL); Yossi Bar, Haifa (IL); Amir Belson, Savyon (IL); Michael Retter, Tel Aviv (IL)

(73) Assignee: Radiaction Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/496,686

(22) Filed: Oct. 7, 2021

(65) Prior Publication Data

US 2022/0270773 A1    Aug. 25, 2022

Related U.S. Application Data

(63) Continuation of application No. 16/731,424, filed on Dec. 31, 2019, now Pat. No. 11,152,128.
(Continued)

(51) Int. Cl.
*G21F 3/00* (2006.01)
*G21F 1/08* (2006.01)
*G21F 1/12* (2006.01)

(52) U.S. Cl.
CPC ............... *G21F 3/00* (2013.01); *G21F 1/085* (2013.01); *G21F 1/125* (2013.01)

(58) Field of Classification Search
CPC ............ G21F 3/00; G21F 1/085; G21F 1/125
(Continued)

(56) References Cited

U.S. PATENT DOCUMENTS 2,593,526 A    4/1952  Savage et al.
4,034,228 A    7/1977  Arauner
(Continued)

FOREIGN PATENT DOCUMENTS

CN    103045983 B    12/2015
CN    205959627 U    2/2017
(Continued)

OTHER PUBLICATIONS

EP19907256.2 Extended Search Report dated Sep. 1, 2022.
(Continued)

*Primary Examiner* — Nicole M Ippolito
(74) *Attorney, Agent, or Firm* — Wilson Sonsini Goodrich & Rosati

(57) ABSTRACT

The present invention relates to rigid structures and composite materials thereof for providing radiation attenuation/shielding. Some embodiments pertain to a radiation shielding apparatus including: a plurality of positionable radiation-shielding stacks of tiles. The stacks are subsequently and adjacently arranged in a contiguous configuration. A tile positioning mechanism allows movement of tiles within a stack between a stacked (retracted) position and an extended position. In the extended position, the tiles of each of the plurality of radiation shielding stacks at least partially overlap tiles of subsequent and adjacent tile stack at corresponding opposing side-margins thereof.

20 Claims, 15 Drawing Sheets

Related U.S. Application Data

(60) Provisional application No. 62/787,636, filed on Jan. 2, 2019.

(58) Field of Classification Search
USPC ......... 250/505.1, 515.1, 516.1, 517.1, 518.1, 250/519.1
See application file for complete search history.

(56) References Cited

U.S. PATENT DOCUMENTS

| | | |
|---|---|---|
| 4,587,277 A | 5/1986 | Sato |
| 5,099,134 A | 3/1992 | Hase et al. |
| 5,523,578 A | 6/1996 | Herskovic |
| 5,525,408 A | 6/1996 | Weir et al. |
| 6,325,538 B1 | 12/2001 | Heesch |
| 7,897,949 B2 | 3/2011 | Ballsieper |
| 8,113,713 B2 | 2/2012 | Belson et al. |
| 8,439,564 B2 | 5/2013 | Belson et al. |
| 8,460,777 B2 | 6/2013 | Long |
| 11,006,909 B2 | 5/2021 | Yifat et al. |
| 11,152,128 B2 * | 10/2021 | Yifat ...................... A61B 6/107 |
| 2003/0174802 A1 | 9/2003 | Hare |
| 2004/0029998 A1 | 2/2004 | Tomita et al. |
| 2017/0278585 A1 | 9/2017 | Almer et al. |
| 2018/0168525 A1 | 6/2018 | Belson et al. |
| 2018/0249972 A1 | 9/2018 | Yifat et al. |

FOREIGN PATENT DOCUMENTS

| | | |
|---|---|---|
| JP | 6391149 B2 | 9/2018 |
| WO | WO-2017083437 A1 | 5/2017 |
| WO | WO-2020142556 A1 | 7/2020 |

OTHER PUBLICATIONS

International Search Report and Written Opinion for PCT/US2019/069154 dated Mar. 5, 2020.
Office action dated Dec. 10, 2020 for U.S. Appl. No. 16/731,424.
U.S. Appl. No. 16/731,424 Notice of Allowance dated Jun. 17, 2021.

* cited by examiner

RADIATION PROTECTION APPARATUS AND MATERIALS THEREFOR

CROSS-REFERENCE

This application is a continuation of U.S. patent application Ser. No. 16/731,424, filed Dec. 31, 2019, now U.S. patent Ser. No. 11,152,128, which claims priority from provisional patent application U.S. 62/787,636, filed Jan. 2, 2019, the entire content of which is incorporated herein by reference.

FIELD OF THE INVENTION

The present invention relates to rigid structures and composite materials thereof providing radiation attenuation/shielding. Some embodiments of the invention pertain to a radiation shielding apparatus comprising: a plurality of positionable radiation-shielding stacks of tiles, wherein the stacks are subsequently and adjacently arranged in a contiguous configuration of stacks; and a tile positioning mechanism configured to allow movement of tiles within a stack between a stacked or retracted position and an extended position, wherein in the extended position, the tiles of each of the plurality of radiation shielding stacks partially overlap tiles of subsequent and adjacent tile stack at corresponding opposing side-margins thereof.

BACKGROUND OF THE INVENTION

X-ray equipment is routinely used in various applications and systems, including as a diagnostic tool in medical settings. As a result, health care providers and technical personnel who operate X-ray systems may be exposed to cumulative dosage of radiation and may be harmed by such X-ray exposure. Thus, in the field and art of medical imaging, there is an on-going need for improved equipment design, materials and methodologies for preventing or at least minimizing such cumulative radiation exposure, to reduce health risks. X-ray shielding equipment is part of this effort to reduce exposure from stray radiation to below specified levels.

Exemplary teachings in the field and art of the invention are provided by the applicant of the present invention in the following disclosures: U.S. Pat. Nos. 8,439,564 and 8,113,713, and WO 2017/083437, which are incorporated by reference as if fully set forth herein.

Additional disclosures in this field include: U.S. Pat. Nos. 6,325,538; 8,460,777; 7,897,949; 5,525,408; 5,099,134; US 2003/174802; US 2017/278585; JP 6391149; CN 2059596270; and CN 103045983, which are incorporated by reference as if fully set forth herein.

Exemplary radiation shielding apparatuses are described in the following disclosures: US patent application Nos. 2018/0168525, and 2018/0249972, and are incorporated by reference as if fully set forth herein.

Among the challenges associated with radiation shielding equipment is the requirement to maintain as complete a shielding as possible, preferably using materials that are low weight yet rigid and have sufficient radiation shielding/blocking properties.

SUMMARY OF THE INVENTION

The present invention relates to a radiation shielding apparatus including adjacent stacks of radiation shielding tiles that can be extended for radiation shielding of an area outside the apparatus or at least mitigate the exposure to scattered radiation. Such shielding is intended to limit/reduce radiation exposure to personnel and technicians who work with and near X-ray radiation systems (e.g., a C-arm of a fluoroscopy system).

The present invention provides an apparatus having stacks of tiles with a tile positioning mechanism that allows moving the tiles between a retracted stacked position and an extended position. The tiles have a unique structure which provides compact contracted arrangement when the tiles are in the retracted position and minimizes leakage of radiation when the tiles are in the extended position. The tiles include side margins with a unique structure for mitigating radiation leakage.

As such, the apparatus may include at least one radiation shield assembly including a support base operatively connectable to a radiation source or a radiation detector of an X-ray system;

a plurality of positionable radiation-shielding stacks of tiles, wherein the stacks are subsequently and adjacently arranged in a contiguous configuration of stacks; and a tile positioning mechanism configured to allow movement of tiles within a stack between a stacked or retracted position and an extended position, wherein in the extended position, the tiles of each of the plurality of radiation shielding stacks at least partially overlap tiles of subsequent and adjacent tile stack at corresponding opposing side-margins thereof.

The tiles may include a composite radiation shielding material. This composite material allows the apparatus to be low weight, yet rigid, and still provide for radiation shielding. Structures including the herein disclosed composite materials may be configured in various combinations of material components; various layers, and/or combination of layers, and/or permutations of layers; and as flat, or non-flat, depending upon implementations thereof.

A particular example of a non-flat configuration is at one or both side-margins of the tiles, which can be particularly useful for mitigating radiation leakage. Configurations of such side-margins may include a V-shaped portion, a wavy configuration and/or a zig-zag pattern, or a combination thereof. Such configurations (e.g. wavy and zig-zag) allow stable and overlap of increased surface area of the side-margins of adjacent tiles, without using/requiring additional linear space; and provide a more tortuous path for radiation to potentially leak thereby reducing the chances and/or amount of radiation leakage. The edges (peak of ridges) of the V-shape or zig-zags (and crests/valleys of the waves) define an axis A1 parallel to the extension direction of the tile stacks. Namely, edges (peak of ridges) are parallel to the direction of movement of the tile stacks.

Advantages of the present invention may include (a) a reduction in radiation exposure (i.e. providing a more comprehensive a radiation shield), which may in particular include reducing radiation leakage at the corners of the radiation shield; (b) improvement in the overlap of adjacent radiation shielding tiles or tile-stack segments (i.e. stacks of tiles) to thereby mitigate radiation leakage; and (c) provide for improved strength and/or stability of the radiation shield. Examples of improved configurations or patterns of such overlap are noted above, namely wavy; V-shape, and zig-zag. Again, regardless of the particular shape of the tile's edge-margins, or whether the tiles form a face of the shielding structure or include corners thereof, the edges (peak of ridges) of the V-shapes or zig-zags and/or crests/ valleys of the waves, at the overlapping side-margins, define an axis A1 parallel to the extension direction of the tile stacks.

Thus, an aspect of the invention pertains to a radiation shielding apparatus comprising:

a plurality of positionable radiation-shielding stacks of tiles, wherein the stacks are subsequently and adjacently arranged in a contiguous configuration of stacks; and a tile positioning mechanism configured to allow movement of tiles within a stack between a stacked or retracted position and an extended position, wherein in the extended position the tiles of each of the plurality of radiation shielding stacks at least partially overlap tiles of subsequent and adjacent tile stack at corresponding opposing side-margins thereof.

In one or more embodiments, the tiles and corresponding opposing side-margins are non-flat.

In one or more embodiments, the non-flat corresponding opposing side-margins have a zig-zag or V-shaped profile.

In one or more embodiments, the non-flat corresponding opposing side-margins have a wavy or S-shaped profile.

In one or more embodiments, the stacks of tiles form a structure having at least two faces, each face including at least one tile stack; and corner tile stacks connecting two adjacent faces thereof.

In one or more embodiments, the stacks of tiles form a structure having at least three faces, each face including at least one tile stack; and corner tile stacks connecting two adjacent faces thereof.

In one or more embodiments, the stacks of tiles form a structure having four faces, each face including at least one tile stack; and four corner tile stacks connecting two adjacent faces thereof.

In one or more embodiments, corner tile stacks cover an area of at least about 90° angle between two adjacent faces.

In one or more embodiments, the tile positioning mechanism includes a rail and a slide element for allowing sliding of slide element of one tile along a length of the rail of an adjacent (upper or lower) tile within a stack.

In one or more embodiments, the rails and slide elements within a stack arranged in a graded structural form, thereby providing a compact structure of tiles in a stack.

In one or more embodiments, the rails and slide elements within a stack arranged in a nesting structural form, thereby providing a compact structure of tiles in a stack.

In one or more embodiments, tiles within a stack include a recess to accommodate therein a rail of the tile and a respective slide element of a sequentially adjacent tile.

In one or more embodiments, the recesses of stackedly adjacent tiles of the stack are arranged such that the recess of one tile is correspondingly disposed relative the recess of its sequentially adjacent tile, such that one recess of one tile accommodates at least partially a second recess of a second adjacent tile, thereby providing for a compact structure of tiles in a stack.

In one or more embodiments, each tile comprises a first side margin with a concave or V-shaped profile and an opposite second side margin with a convex or upside down V-shaped profile, and the tiles of subsequent and adjacent tile stacks are arranged such that the concave or V-shaped profile of the tiles within one stack overlap the convex upside down V-shaped profile of the tiles within the subsequent and adjacent tile stack.

The materials and structures of the tiles may include one or more layers of carbon fiber and a binding material, and one or more layers of a radiation attenuation material. In some designs, the herein disclosed tiles include one or more layers of carbon fibers incorporated within a mixture of a binding material and one or more radiation attenuation material. In some designs, the herein disclosed tiles include one or more layers of radiation-attenuating material and a polymer mixture. The structures obtained from the herein disclosed materials are rigid, low-weight, and can be flat or non-flat and possess radiation shielding properties.

An aspect of the invention pertains to rigid/semi-rigid structures comprising a radiation attenuating composite material, the composite material comprising a mixture of one or more polymers and one or more radiation attenuating material(s) wherein the obtained structure is a monolayered structure.

In one or more embodiments, the radiation attenuating material(s) is provided as a powder which is substantially homogenously dispersed in the one or more polymers.

A further aspect of the invention pertains to a radiation attenuating composite material, the composite material comprising: one or more carbon fiber layers; a binding material; and a radiation attenuating material applied onto and/or between the one or more carbon fiber layers.

Yet a further aspect of the invention pertains to a radiation attenuating composite material, comprising: one or more layers of carbon fibers and a binding material; and a radiation attenuating material applied onto and/or between the one or more of carbon fiber layers.

Yet a further aspect of the invention pertains to a radiation attenuating composite material, comprising: one or more layers of carbon fibers; a binding material applied onto and/or between the one or more layers of carbon fibers and configured to at least partially adhere thereto; and a radiation attenuating material applied onto and/or between the one or more carbon fiber layers.

Yet a further aspect of the invention pertains to structures obtained from the herein disclosed radiation attenuating composite materials. Yet a further aspect of the invention pertains to radiation shielding apparatuses obtained from the herein disclosed radiation attenuating structures.

In one or more embodiments, the herein disclosed structures include a binding material. In one or more embodiments, the herein disclosed structures do not include a binding material.

In one or more embodiments, the binding material is a polymer.

In one or more embodiments, the binding material is selected from a thermoset resin, polyester, vinyl ester, nylon, and a combination thereof. In one or more embodiments, the thermoset resin is epoxy resin. In one or more embodiments, the herein disclosed structures do not include a binding material selected from a thermoset resin, polyester, vinyl ester, nylon, and a combination thereof. In one or more embodiments, the thermoset resin is epoxy resin. In one or more embodiments, the herein disclosed structures do not include a thermoset resin.

In one or more embodiments, the herein disclosed structures do not include a carbon fiber.

In one or more embodiments, the radiation attenuating material is a metal. In one or more embodiments, the radiation attenuating material is a metal selected from tungsten, lead, bismuth, antimony, barium, tantalum, and a combination thereof.

In one or more embodiments, the composite material further includes a material selected from aramid (e.g. Poly-paraphenylene terephthalamide and the like, which may be known by the trade names Kevlar, Nomex, Technora, and Twaron), aluminum, ultra-high-molecular-weight polyethylene (UHMWPE), glass fibers, and a combination thereof.

In one or more embodiments, the binding material and the radiation attenuating material are provided as a liquid or semi-solid substantially homogenous mixture comprising particulates of the radiation attenuating material and the binding material.

In one or more embodiments, the radiation attenuating material has a form of a foil. In one or more embodiments, the composite material is arranged as a layered structure comprising one or more layers of the carbon fibers and the binding material and one or more layers of the radiation attenuating material.

In one or more embodiments, the composite material has radiation attenuating capacity that is equivalent to or greater than the attenuating capacity of a lead foil having a thickness of 0.1 mm.

In one or more embodiments, a layer of the radiation attenuating material has radiation attenuating capacity that is equivalent to or greater than the attenuating capacity of a lead foil having a thickness of 0.1 mm.

In one or more embodiments, a layer of the carbon fiber has a thickness of at least about 0.05 mm.

In one or more embodiments, the carbon fibers define the outer surface of the layered structure. In one or more embodiments, at least two adjacent layers of the carbon fibers are spaced apart or separated from each other by the radiation attenuating material. In one or more embodiments, the composite material comprises a first and a second layer of carbon fibers, a third layer of the radiation attenuating material, and a third and fourth layers of carbon fibers. In one or more embodiments, the radiation attenuating material layer is disposed between the carbon fiber layers.

In one or more embodiments, the composite material comprises one or more layers of the carbon fibers onto which the substantially homogenous composition is applied.

In one or more embodiments, the substantially homogenous composition comprises 15% to 95% by weight of the radiation attenuating material and a binding material. In one or more embodiments, the substantially homogenous composition comprises 15% to 60% by weight of the radiation attenuating material and a binding material. In one or more embodiments, the substantially homogenous composition comprises 15% to 80% by weight of the radiation attenuating material and a binding material.

In one or more embodiments, the composite material comprises four layers of the carbon fibers onto which the substantially homogenous composition is applied.

In one or more embodiments, following curing (e.g., by heating, by applying a high pressure, or by simple drying in the ambient environment) a rigid, low-weight, and radiation attenuating product is obtained having a thickness of at least about 0.3 mm.

In one or more embodiments, the composite material comprises two or more types of radiation attenuating material.

In yet a further aspect, the invention provides a rigid structure produced by the radiation attenuating composite materials as herein described. In one or more embodiments, the structure has radiation shielding properties. In one or more embodiments, the structure is a rigid tile. In one or more embodiments, the structure is a non-flat rigid structure. In one or more embodiments, the structure is curved. In one or more embodiments, the tile includes one or more curves for accommodating a sliding mechanism. In one or more embodiments, the sliding mechanism includes a rail. In one or more embodiments, the rail is linear. In one or more embodiment, the sliding mechanism includes a slide element that can slide along a sliding mechanism, or a rail. In one or more embodiments, the sliding mechanism includes a friction regulator element, or a bearing element (e.g., a ball bearing) or the alike.

In yet a further aspect, the invention provides a substantially homogenous radiation attenuating composition comprising a binding material and particulates of one or more radiation attenuating material.

In one or more embodiments, the binding material is selected from a thermoset resin, polyester, vinyl ester, nylon, and a combination thereof. In one or more embodiments, the thermoset resin is epoxy resin. In one or more embodiments, the radiation attenuating material is a metal selected from tungsten, lead, bismuth, antimony, barium, tantalum, and a combination thereof.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Some embodiments of the invention are herein described, by way of example only, with reference to the accompanying drawings. With specific reference now to the drawings in detail, it is stressed that the particulars shown are by way of example and for purposes of illustrative presentation of embodiments of the invention. In this regard, the description taken with the drawings makes apparent to those skilled in the art how embodiments of the invention may be practiced.

In the drawings:

FIG. 1 is a perspective view of a portion of an X-ray system, mainly an exemplary C-arm thereof, including a prior art radiation shielding apparatus.

FIG. 2 is a perspective view of a portion of a radiation protection/shielding apparatus according to embodiments of the present invention.

FIG. 3 is a perspective view of two subsequent and adjacent stacks of radiation-blocking tiles of the present apparatus, in a retracted position, having an extension-retraction or tile-positioning mechanism therefor.

FIG. 4 is a perspective view of two subsequent and adjacent stacks of radiation-blocking tiles of the present apparatus, in an extended position, having an extension-retraction or tile-positioning mechanism therefor.

FIG. 5 is a top view of a stack of three radiation-blocking tiles of the herein apparatus in a retracted position.

FIG. 6 is a perspective view of FIG. 5

FIG. 7 is a top view of a stack and a subsequent and adjacent corner stack, each having four radiation-blocking tiles of the herein apparatus in a retracted position.

FIG. 8 is a top view of a stack and a subsequent and adjacent stack, each having radiation-blocking tiles with side-margins having a zig-zag profile.

FIG. 9 is a top view of a stack and a subsequent and adjacent stack, each having radiation-blocking tiles with side-margins having an S profile.

Figure 10:
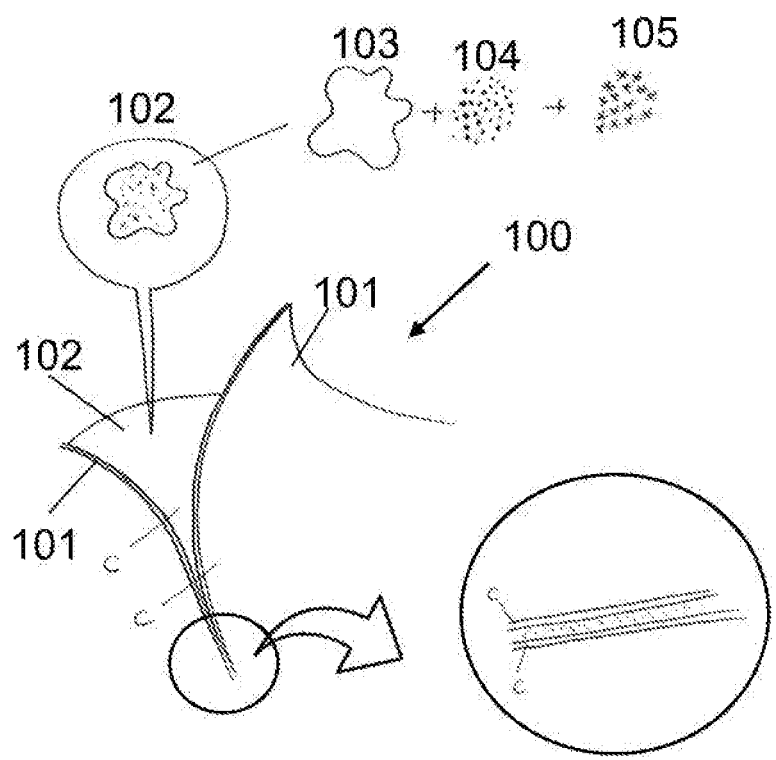

FIG. 10 schematically illustrates a composite material comprising external carbon fiber layers and a middle layer of a substantially homogenous composition comprising a binding material, a first radiation attenuating material and a second radiation attenuating material.

Figure 11:
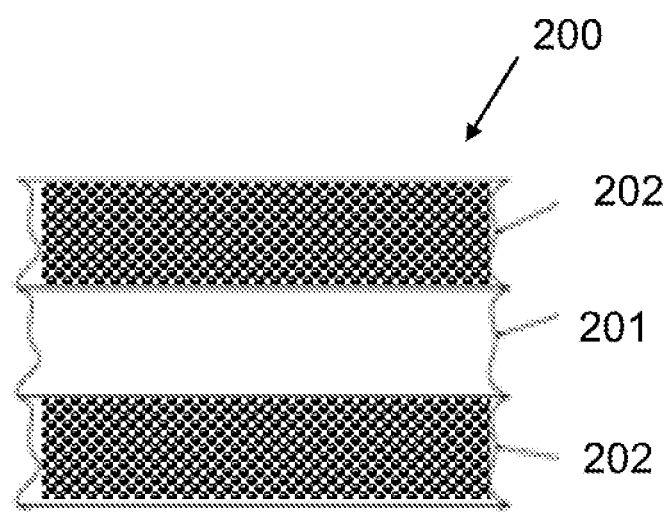

FIG. 11 schematically illustrates an exemplary composite material comprising one layer of carbon fiber incorporated with a substantially homogenous composition comprising a binding material, a first radiation attenuating material and/or a second radiation attenuating material.

Figure 12:
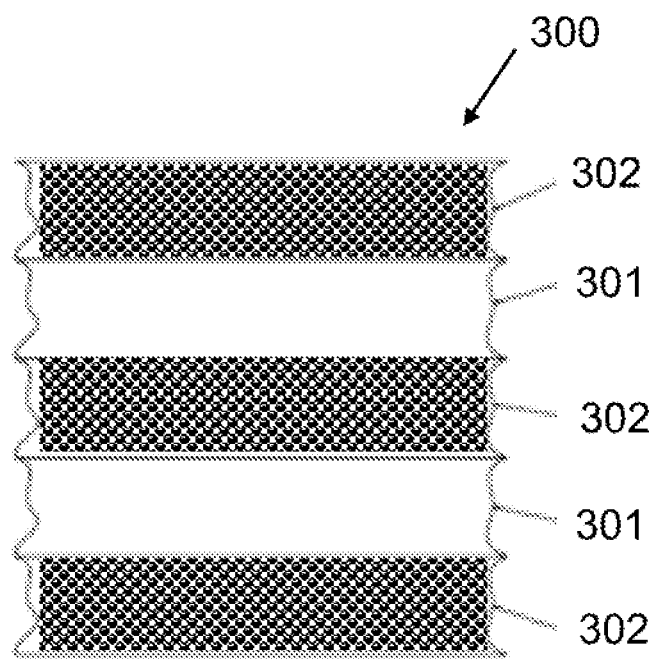

FIG. 12 schematically illustrates an exemplary composite material comprising two layers of carbon fiber, each incorporated with a substantially homogenous composition comprising a binding material, a first radiation attenuating material and/or a second radiation attenuating material.

Figure 13:
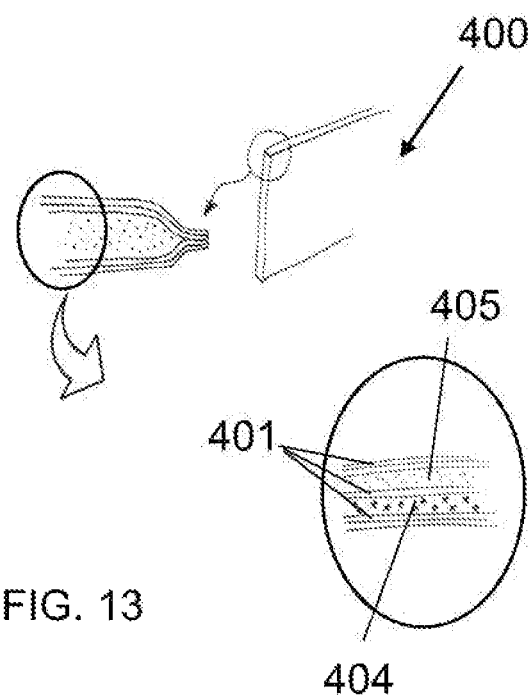

FIG. 13 schematically illustrates an exemplary composite material comprising three carbon fiber layers making a sandwich structure with a first radiation attenuating material and a second radiation attenuating material.

Figures 14A, 14B:
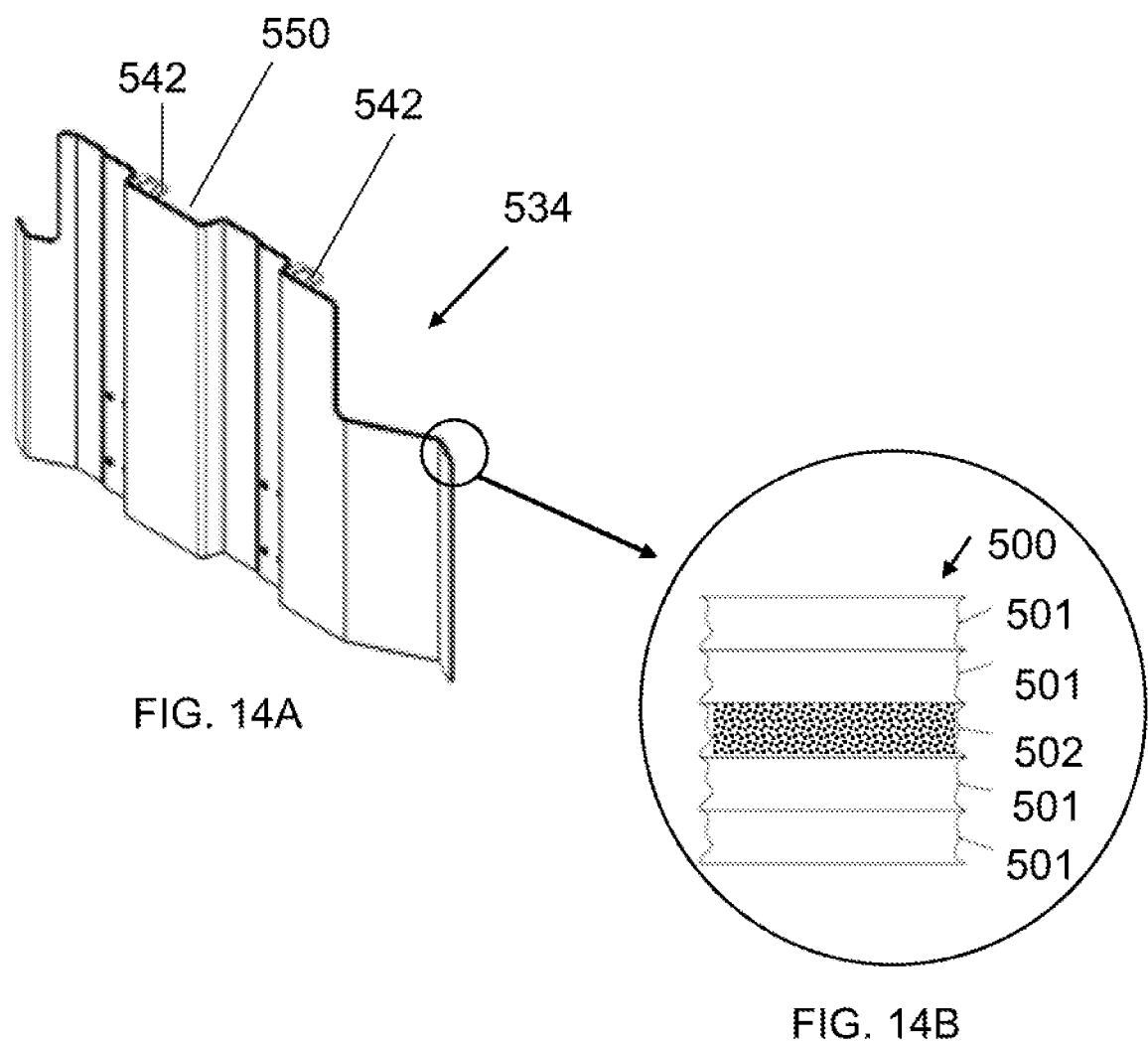

FIGS. 14A-14B schematically illustrate an exemplary tile structure (FIG. 14A) manufactured from a composite material (FIG. 14B) comprising four layers of carbon fiber and a binding material, each two layers spaced apart by a middle layer of a radiation attenuating material, according to some embodiments of the invention.

Figure 15:
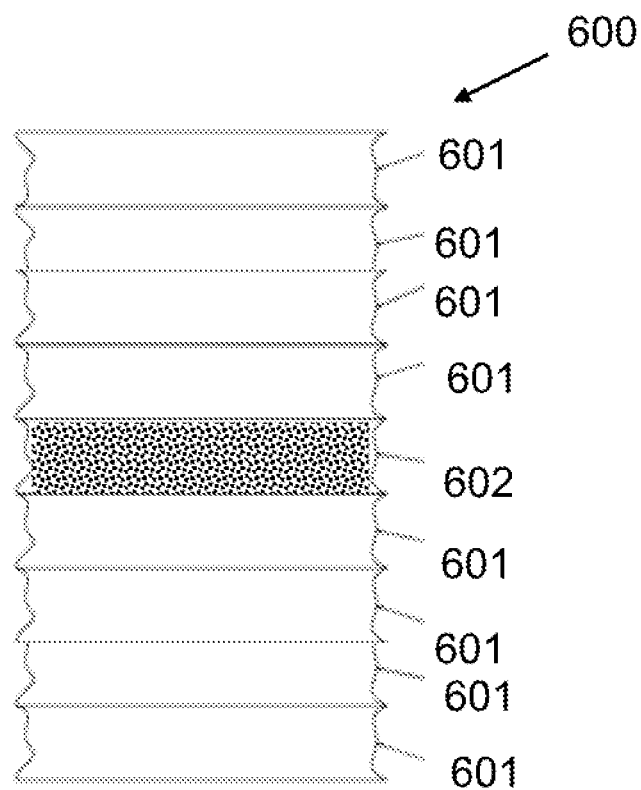

FIG. 15 schematically illustrates an exemplary composite material comprising eight layers of carbon fiber and a binding material, each four layers spaced apart by a middle layer of a radiation attenuating material.

Figure 16:
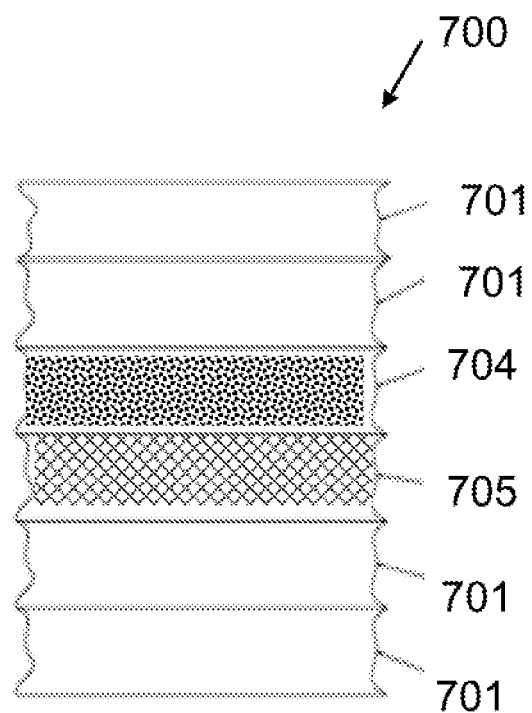

FIG. 16 schematically illustrates an exemplary composite material comprising four layers of carbon fibers and a binding material, each two layers spaced apart by a dual middle layer having a layer of a first radiation attenuating material and a layer of a second radiation attenuating material.

Figure 17:
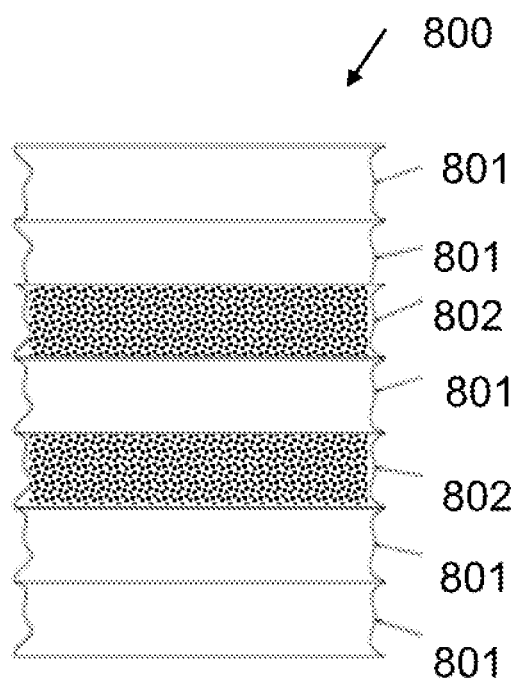

FIG. 17 schematically illustrates an exemplary composite material comprising four layers of carbon fibers and a binding material, each two layers spaced apart by a triple middle layer having a layer of a first radiation attenuating material, a layer of a second radiation attenuating material and in between a layer of carbon fiber.

Figure 18:
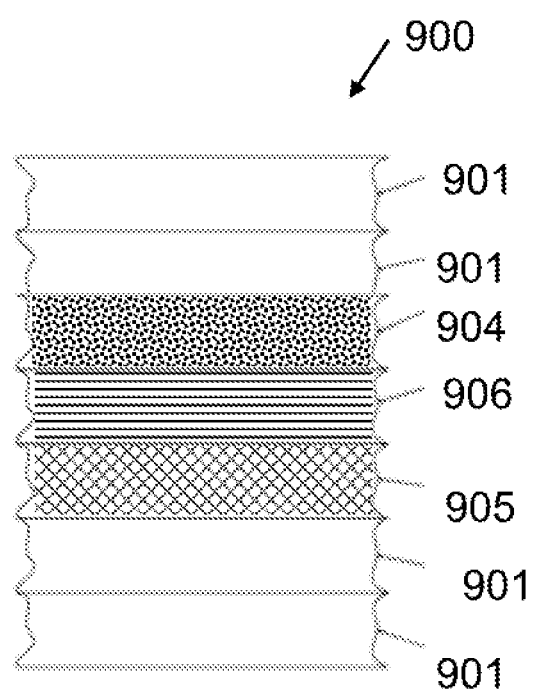

FIG. 18 schematically illustrates an exemplary composite material comprising four layers of carbon fibers and a binding material, each two layers spaced apart by a triple middle layer that includes a layer of a first radiation attenuating material, a layer of a second radiation attenuating material, and in between a spacer layer.

Figures 19A, 19B:
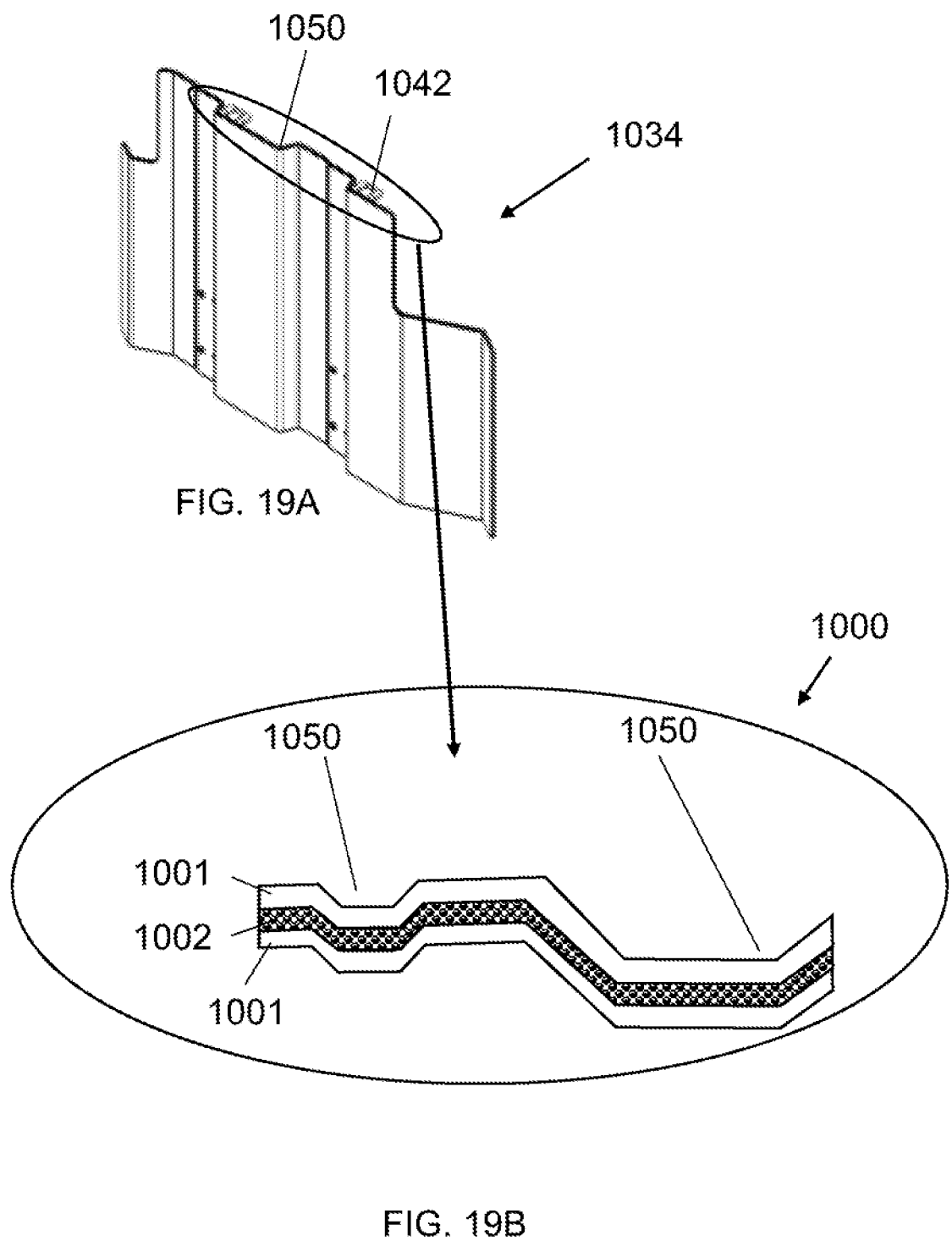

FIGS. 19A-19B schematically illustrate an exemplary curved tile structure (FIG. 19A) used as a shielding element in a radiation shielding apparatus that blocks radiation emitted from an X-ray imaging system; the tile manufactured from a composite material (FIG. 19B) having two layers of carbon fibers and a binding material and a middle layer of a radiation attenuating material.

Figures 20A, 20B:
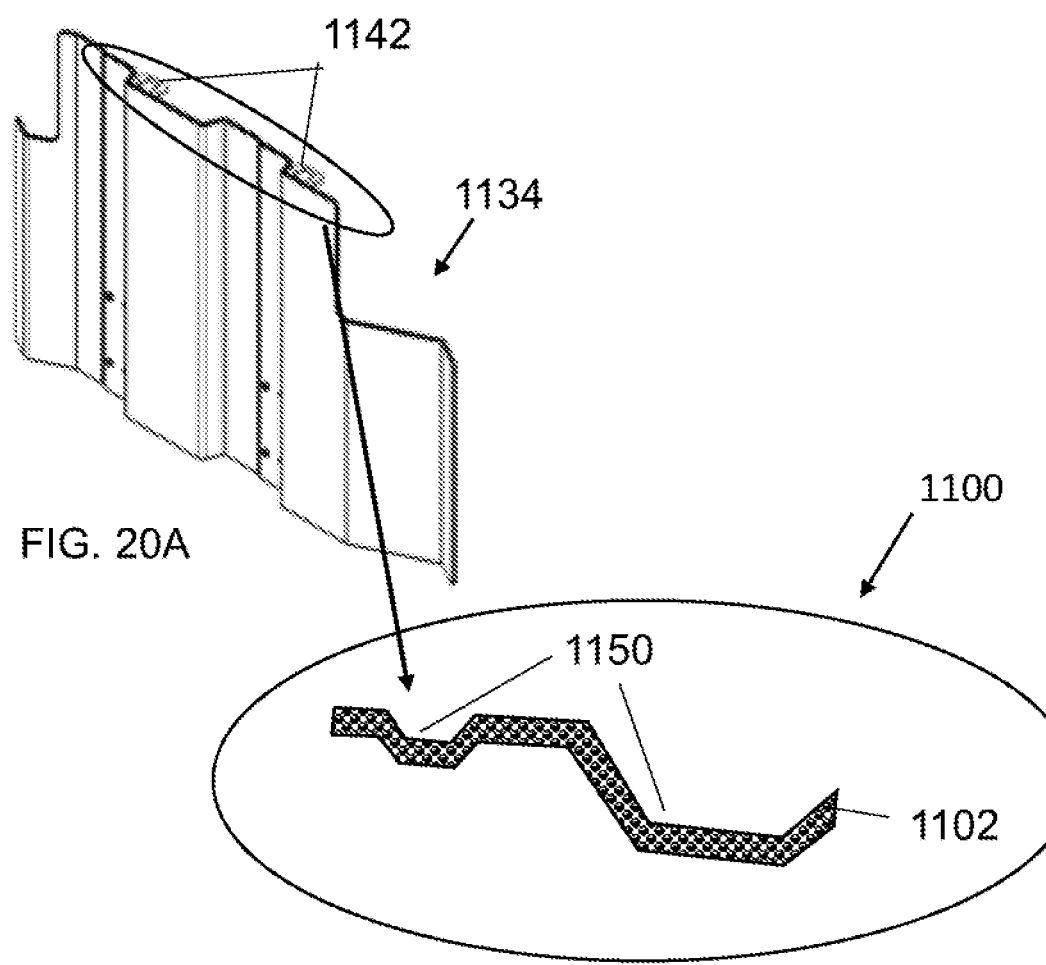

FIGS. 20A-20B schematically illustrate an exemplary curved tile structure (FIG. 20A) manufactured from a composite material (FIG. 20B) having a single layer composition of a radiation attenuating material and a polymeric material.

It should be appreciated that for simplicity and clarity of illustration, elements shown in the figures have not necessarily been drawn to scale. For example, the dimensions of some of the elements are exaggerated relative to each other for clarity. Further, where considered appropriate, reference numerals have been repeated among the figures to indicate corresponding elements.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

It is understood that the invention is not limited to the particular methodology, devices, items or products etc., described herein, as these may vary as the skilled artisan will recognize. It is also to be understood that the terminology used herein is used for the purpose of describing particular embodiments only and is not intended to limit the scope of the invention. The following exemplary embodiments may be described in the context of radiation shielding apparatus and portions thereof for ease of description and understanding. However, the invention is not limited to the specifically described products and methods and may be adapted to various applications without departing from the overall scope of the invention. All ranges disclosed herein include the endpoints. The use of the term "or" shall be construed to mean "and/or" unless the specific context indicates otherwise.

The present invention pertains to radiation shielding apparatuses and devices that can be incorporated into radiation emitting systems (e.g. X-ray systems) so as to surround the radiation/X-ray source and/or image intensifier, thereby protecting the surroundings from exposure to scattered radiation.

The term "X-ray" and its derivatives may be used interchangeably herein with the term "radiation" and its derivatives; although for the most part the term "X-ray" will be used for ease of understanding and readability, however, without intention to limit the scope of the invention.

Features of the present invention pertain to radiation radiopaque tiles (or segments holding these tiles) useful in forming a contiguous shield of a radiation shielding apparatus. The radiation shielding apparatus formed from the herein disclosed tiles are useful in providing protection of the surroundings from exposure to scattered radiation emitted by X-ray systems during fluoroscopic imaging procedures.

The radiation shielding apparatus/device of the invention includes an assembly of sequentially arranged stacks of radiation-blocking tiles. Each stack includes a plurality of tiles. The stacks/segments are sequentially arranged with and movably connected to (associated with) each other to form an extendable and contactable tile stack having a plurality of tiles wherein each two adjacent stacks and their tiles partially overlap forming a contiguous radiation shield.

The herein disclosed tiles include at (or included in) side-margins thereof extensions to form segments/stacks having a plurality of tiles wherein the extensions (or side margins) of tiles of one stack are arranged to geometrically match (correspond to) and at least partially overlap the extensions (side-margins) of tiles of an adjacent stack, thereby forming a contiguous radiation shield.

The tiles (in particular the segments) of a tile stack are deployable. In other words, the tiles arranged parallel to each other in a compact/retracted position (see for example FIG. 3) and can be deployed, forming an extended radiopaque barrier (see for example FIG. 4). The tile stacks are also retractable from an extended position, wherein the deployed tiles slide back onto each other, optionally via a sliding mechanism, returning to the compact/retracted position.

In one or more embodiments, the tiles are frame-less, or include no peripheral frame. When in a retracted position, a compact, light-weight segment stack is formed.

The segments are arranged sequentially and include corner segments having corner tiles disposed at corners of the assembly of tile/segment stacks, forming a shape that spans the region of X-ray imaging. The radiation shielding assembly may include at least two faces, at least three faces, at least four faces, or at least five faces. The corner segments with corner tiles may span at least about a 90° angular area between tile-segments of adjacent faces within an assembly of the shielding apparatus, thereby covering an entire corner area. The corner segments with corner tiles may span between about a 90° and about a 120° angular area between tile-stacks of adjacent faces within an assembly of the shielding apparatus, thereby covering an entire corner area. The corner segments with corner tiles may span about a 90° angular area in an exemplary square/rectangular-like assembly, thereby covering an entire corner area between tile-stacks of adjacent faces within an assembly of the shielding apparatus. The corner segments with corner tiles may span about a 108° angular area in an exemplary pentagonal-like assembly, thereby covering an entire corner area between tiles-stacks of adjacent faces within an assembly of the shielding apparatus. The corner segments with corner tiles may span about a 120° angular area in an exemplary hexagonal-like assembly, thereby covering an entire corner area between tile-stacks of adjacent faces within an assembly of the shielding apparatus.

Figure 1:
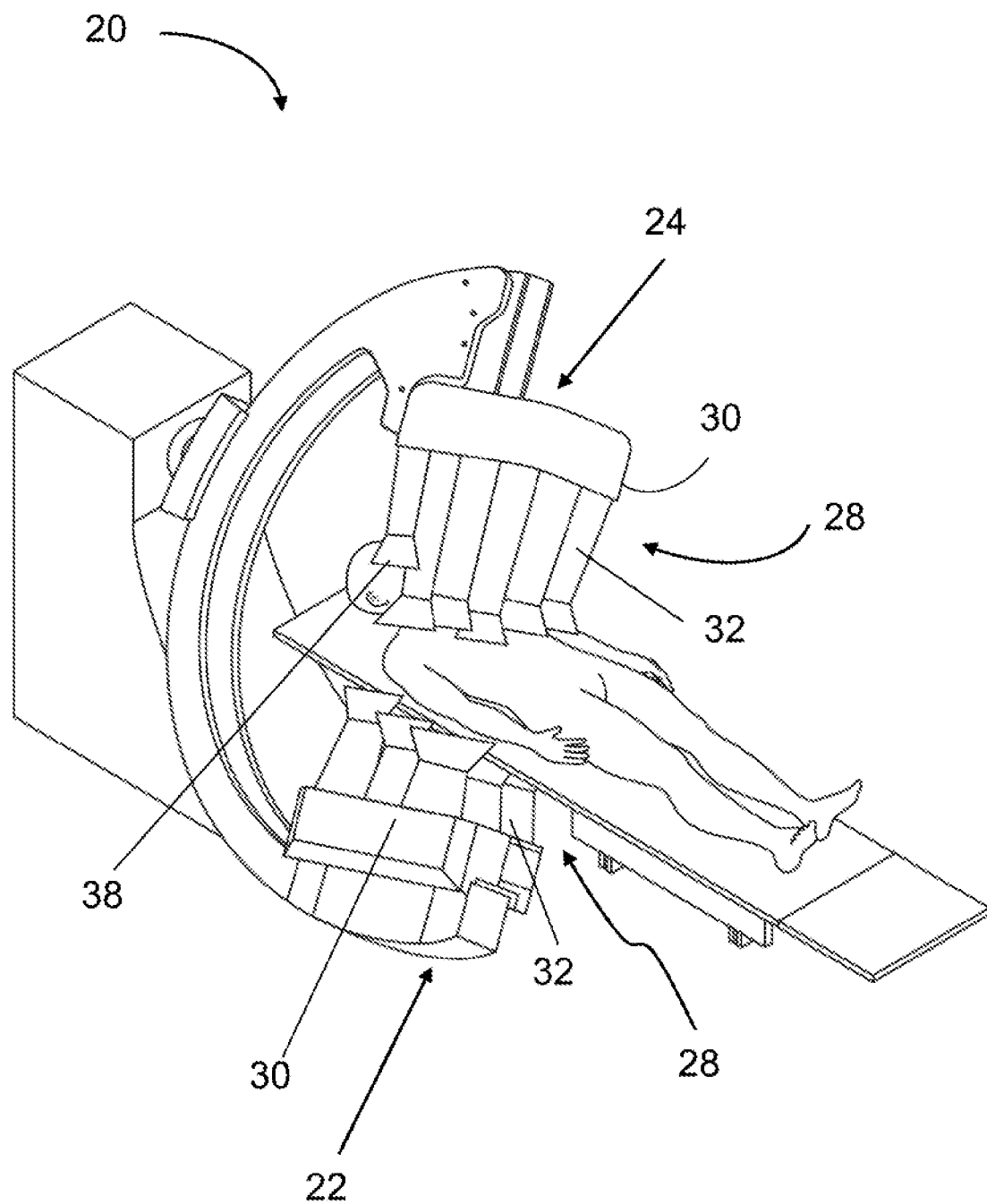

FIG. 1 schematically illustrates a prior art radiation shielding apparatus. The apparatus is shown in conjunction with a typical C-arm 20 of an X-ray system for performing an X-ray image of a patient. The X-ray system includes a radiation source 22 and a radiation detector 24 mounted on opposing ends of C-arm 20. The apparatus includes a radiopaque or radiation attenuating/blocking shield, which includes at least one radiation shield assembly 28 (e.g. above and below the patient, as illustrated) having a support base 30 connectable to radiation source 22 and/or connected to radiation detector 24, which are mounted on opposite ends of C-arm 20.

Figure 2:
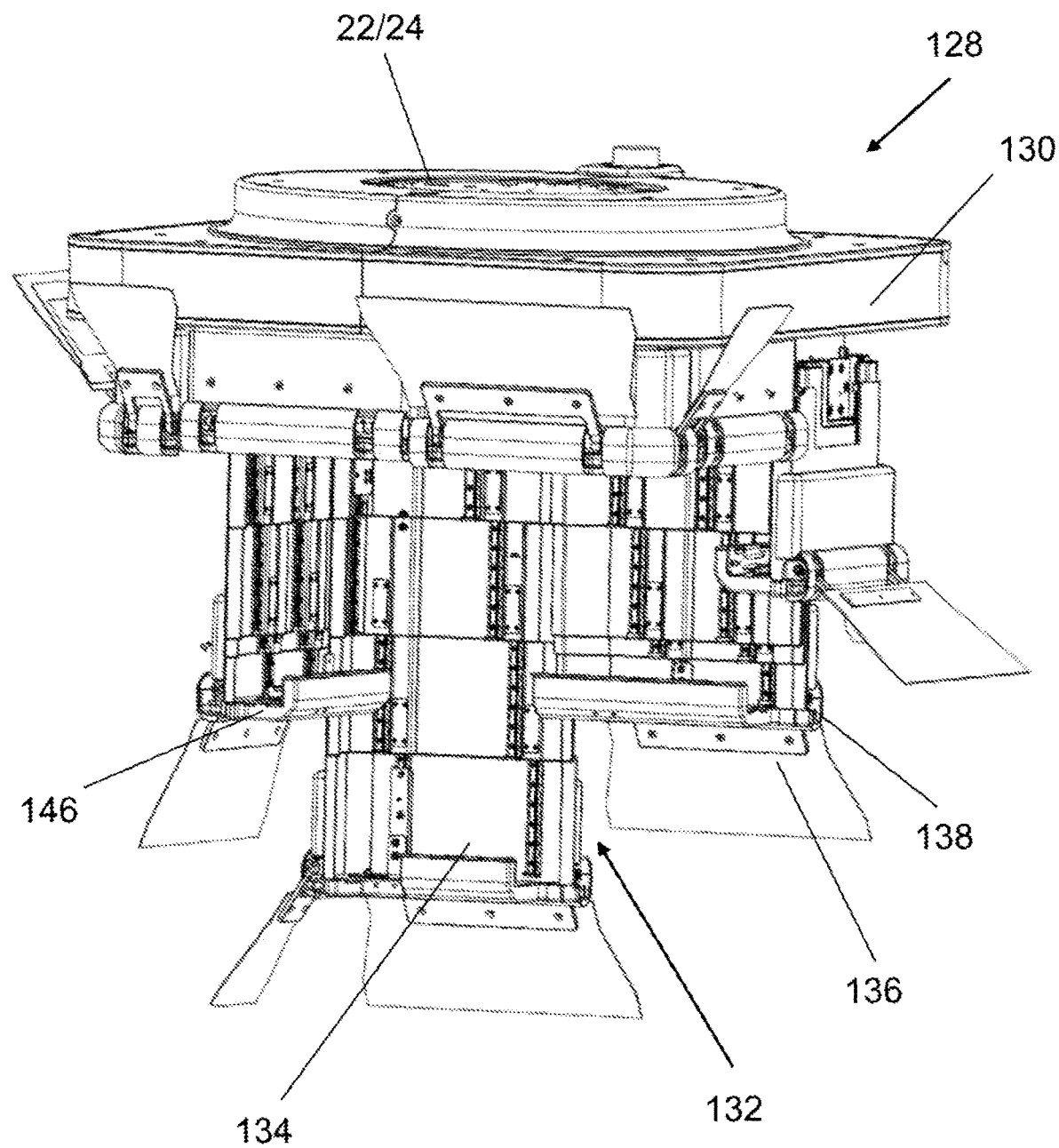

Radiation shield assembly 28 includes a plurality of radiation shield stacks 32, which include a plurality of stack-tiles (such as tiles 134 shown in FIG. 2). These radiation shield stacks 32 are sequentially positioned relative to support base 30, thereby forming radiopaque screen radiation attenuating/blocking shield in a contiguous configuration.

Shield assembly 28 has free ends 38 for spanning the periphery of a body region of the patient. Radiation shield stacks 32 and tiles 134 thereof are controllable to extend or contract to a selected length to position respective free ends 38 in proximity of the patient, or an object such as an X-ray table.

In use, radiation source 22 and radiation detector 24 are positioned at opposite sides of the patient, in particular a specific portion of the patient. Radiation source 22 emits an X-ray beam that passes through the specific portion of the patient toward radiation detector 24, which records the exposure to X-ray radiation and sends the image or video feed to a computer and/or a display.

FIG. 2 schematically illustrates an exemplary radiation shield assembly 128 of the present invention, which constitutes part of a radiation protection apparatus which is operatively connectable to an X-ray system or the like. The radiation shield assembly 128 is operatively connected to a support base 130 which in turn is connectable to a radiation source 22; and/or connectable to a radiation detector 24.

Assembly 128 includes radiation shield stacks 132 (stacks of tiles) sequentially disposed to operably extend from support base 130, thereby forming a contiguous radio-opaque barrier configured for spanning an imaging area during an X-ray procedure. The radiation shield stacks 132 may be individually and actively controllable to extend and retract to a selected length; in other words, respective tiles 134 of the stacks 132 are movable to an extended and retracted position (including partially or fully retracted/extended). Tiles 134 can be considered as constituting or being a part of respective stack segments, and as such, the terms "stack-segments"; "stack-tiles"; and "tiles", and their derivatives, may be used interchangeably throughout the specification and claims. Assembly 128 may also include flaps 136 at free ends 138 of the stacks 132, for example pivotably attached to the free ends, to aid in surrounding the patient and help limit exposure to scattered radiation. Stacks 132 can be attached to support base 130 via the innermost tile 134 as illustrated in FIG. 2. Alternatively, stacks 132 can be attached to support base 130 via the outermost tile 134. Further, a free end 138 of outermost tile 134 is connected to flap 136 via support base 146 and bracket 147.

Figure 3:
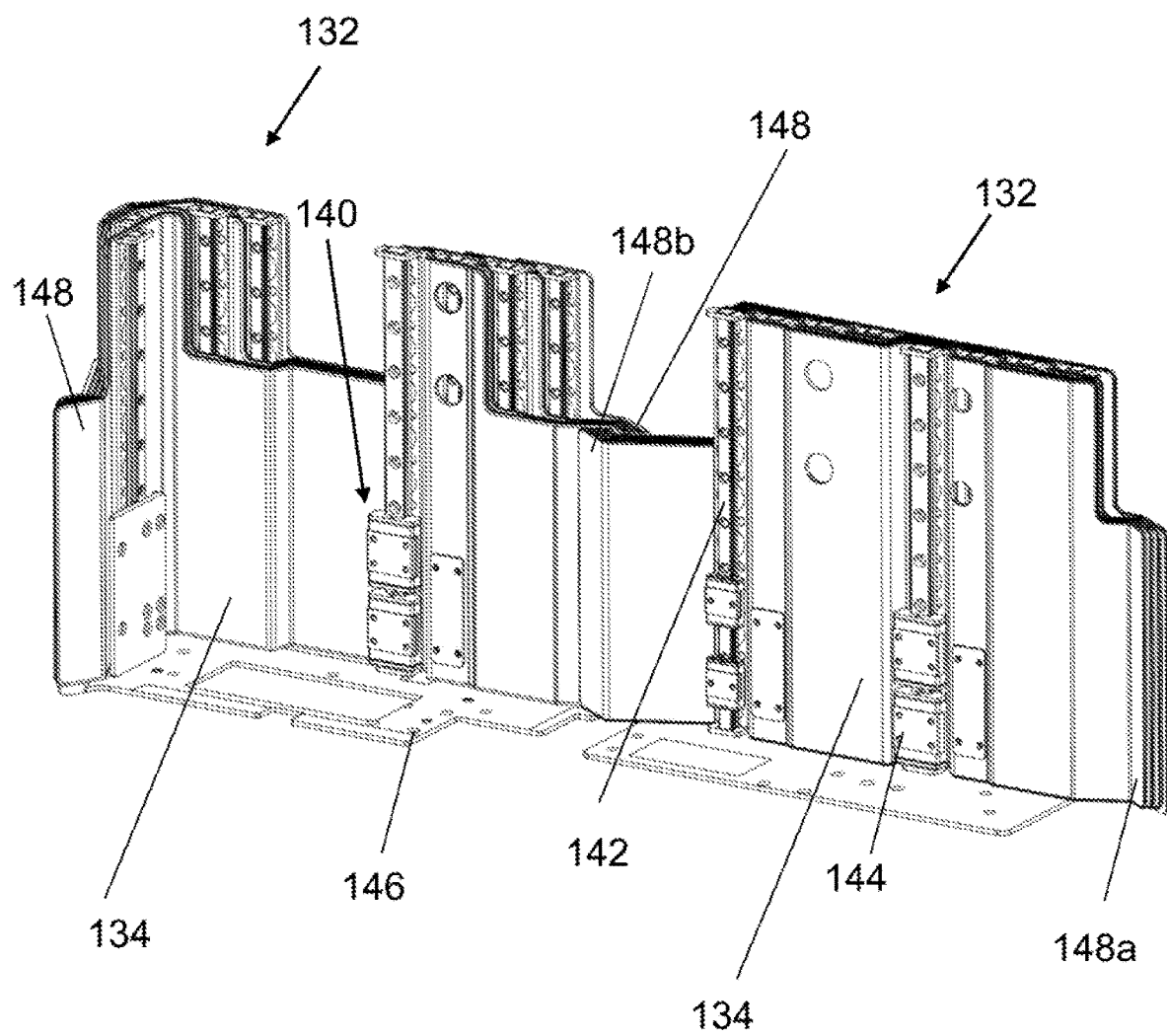
Figure 4:
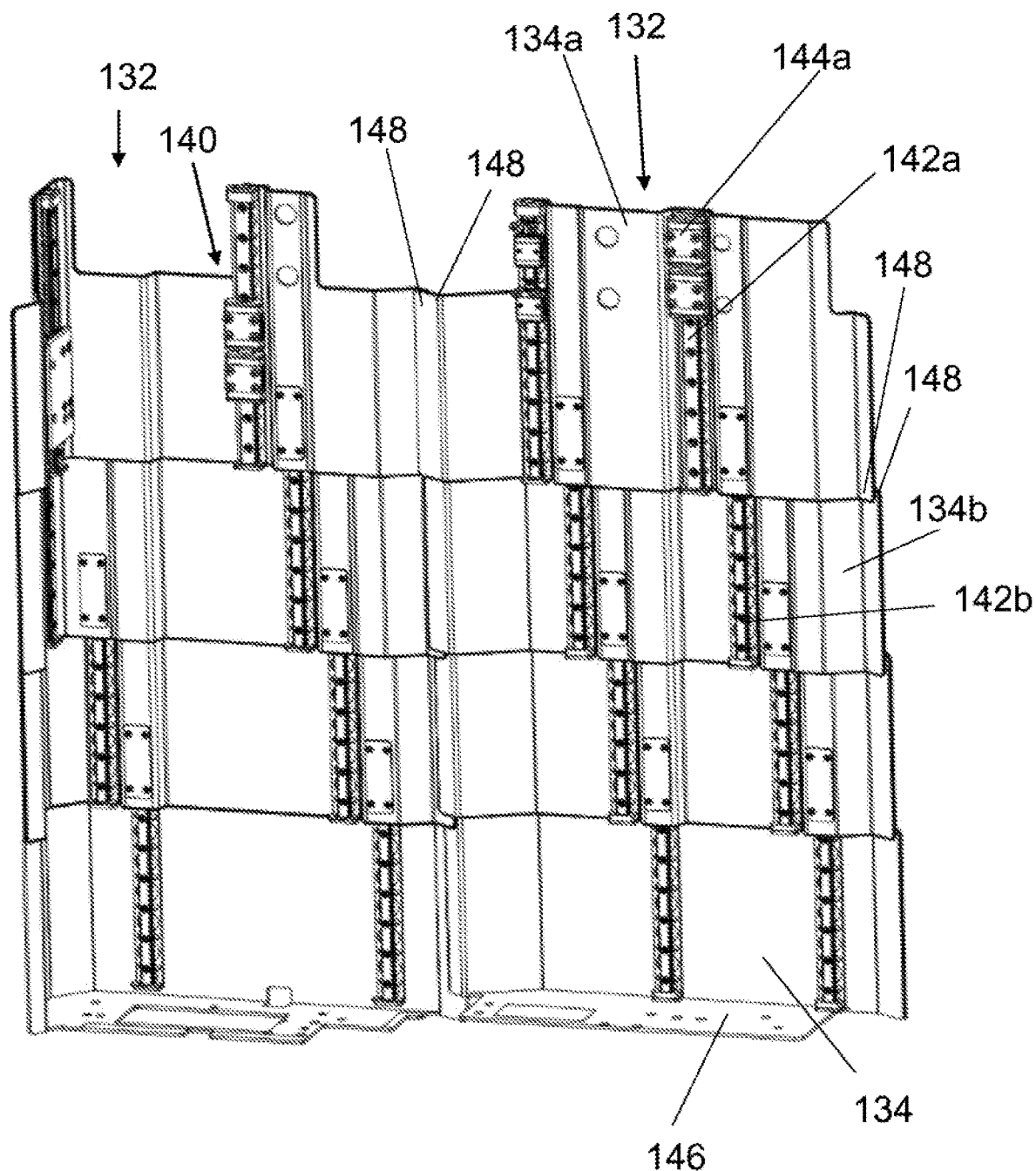

FIGS. 3 and 4 respectively show stack-tiles 134 in a retracted and an extended position; extension and retraction can be performed using a retraction-extension or tile positioning mechanism 140. In the retracted configuration (FIG. 3), tiles 134 are disposed parallel to each other, forming a stacked compact structure. Tile positioning mechanism 140 may include one or more rails 142, which may be linear, as illustrated; and a slide element 144 configured to slide along respective rails 142. Each tile 134 includes at least one rail 142 and at least one slide element 144. Optionally, each tile 134 includes two rails 142 and two slide elements 144. As can be seen in FIG. 4, in order to allow a compact retracted form, the rails 142a of one tile 134a are disposed offset the rails 142b of the other tile 134b. Similarly, in order to allow a compact retracted form, the slide elements 144a of one tile 134a are disposed offset the slide elements (not shown) of the other tile 134b. Namely, the obtained tile positioning mechanism 140 presents a graded structure that facilitates the compact stack structure.

Tile positioning mechanism 140 may include a friction regulator element, or a bearing element (e.g., a ball bearing) or the like, not shown, and may be configured for manual operation, for example simply by pulling and pushing to the desired position, or including a hand crank (which may include a rack and pinion device or a pulley mechanism), not shown. Alternatively or additionally, tile positioning mechanism 140 may further include a powered mechanism including a motor, e.g., an electric motor or a pneumatic or a hydraulic mechanism, not shown.

FIGS. 3 and 4 also illustrate that tiles 134 have tile side-margins 148. Side-margins 148 are critical to providing efficient radiation protection and preferably have a non-flat configuration, for example having one or more generally V-shaped or L-shaped ridges, as illustrated. However, other such configurations, for example a wavy or S-shaped configuration (shown in FIG. 9) is also efficient. FIG. 3 also illustrates how stackedly adjacent side-margins 148 correspond one to the next within each stack 132, as well as between stacks 132 on either side thereof. FIG. 4 also illustrates how side-margins 148 of neighboring tiles 134 of neighboring adjacent stacks 132 correspond, as well as between stackedly adjacent tiles. As shown, each tile 134 includes a concave-like structure 148a (FIG. 3) at a first side-margin of the tile 134 and a convex-like structure 148b at a second opposing side-margin of the tile 134. Such concave-convex structure constitutes a substantially stable shield wherein tiles 134 within stacks 132, when deployed, hold each other, maintaining a stable and contiguous radiation attenuating structure/barrier without any detachment of any of the stacks and/or tiles.

Thus, it should be understood that tiles 134 of one stack 132 are disposed and arranged such that opposing/neighboring lateral sides (side-margins 148) thereof at least partially overlap lateral sides (side-margins) of tiles of an adjacent stack. Similarly, tiles 134 are disposed and arranged such that bottom and upper ends thereof overlap upper and bottom ends of other vertically (stackedly) disposed adjacent tiles of the same stack, as illustrated in FIG. 4. Such an overlap between the bottom and upper ends can be formed by the overlap of elements of the tile positioning mechanism 140. As a result, a contiguous closed and protective shield with minimal radiation leakage is provided to protect from an X-ray radiation scattering during imaging.

Figure 5:
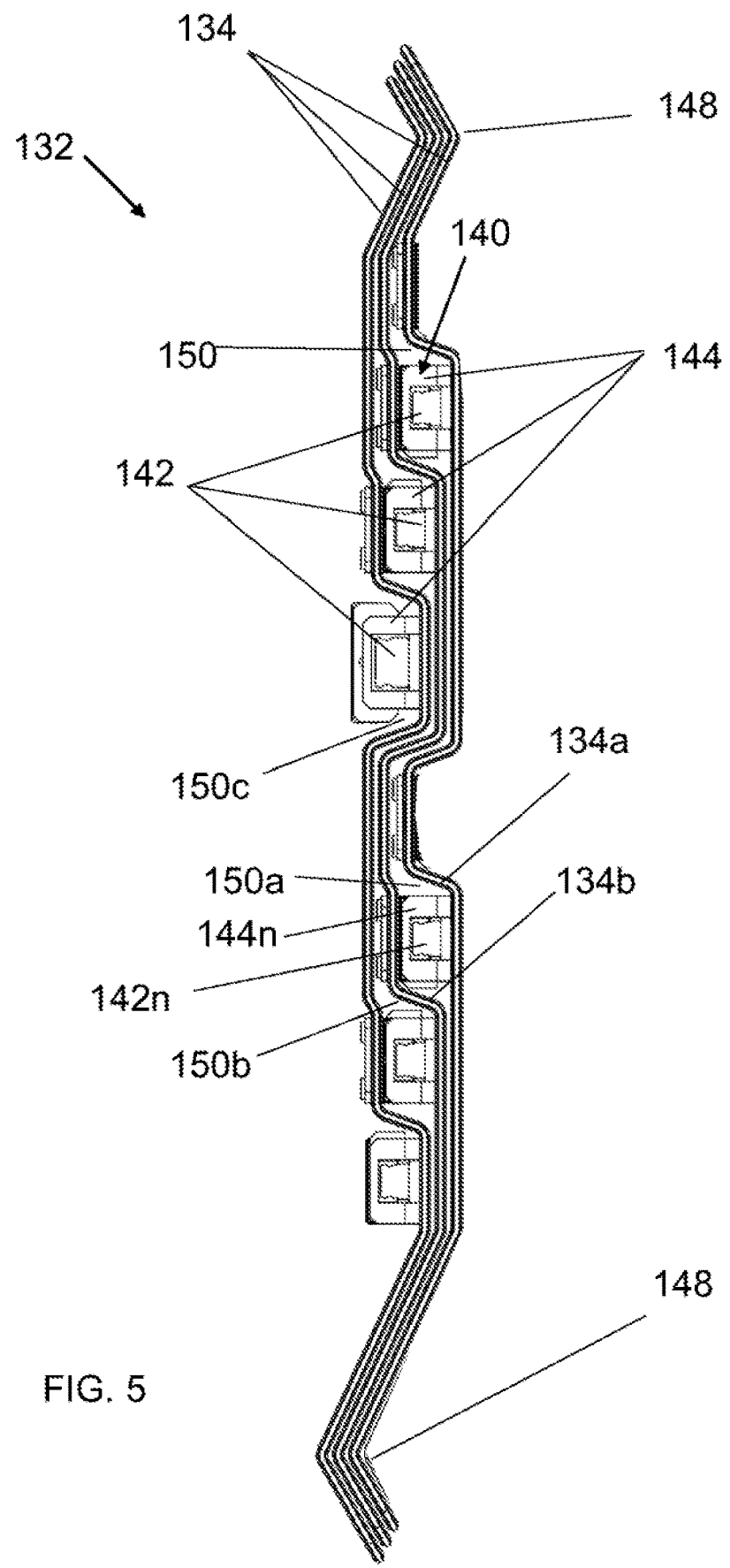

FIG. 5 shows rails 142 and slide elements 144 of tile positioning mechanism 140 disposed and accommodated in one or more indentations or recesses 150 of the tiles 134, in particular in spaces or voids formed by the corresponding recesses in one or more stackably adjacent tiles 134 of each stack 132. The term "stackably" refers to the situation where the tiles 134 are one above (or below) a subsequent tile of the same stack 132 when the tiles are in the retracted position. As a result of the configuration of indentions/recesses 150, adjacent stackable tiles 134 (e.g. tile 134a and tile 134b) are correspondingly configured so as to accommodate a rail 142n and a slide element 144n. Such corresponding configuration may be accomplished by subsequent tiles 134 as illustrated, namely, wherein tile 134b is subsequent to tile 134a and tile 134b has a recess 150b that is narrower than a recess 150a of tile 134a and recess 150b fits within recess 150a, like a smaller/narrower tray fits within a larger/wider tray. In the particular design, the width of recess 150b is about two-thirds of the width of recess 150a; and the width of recess 150c is about one-third of the width of recess 150a, and about half the width of recess 150b.

Figure 6:
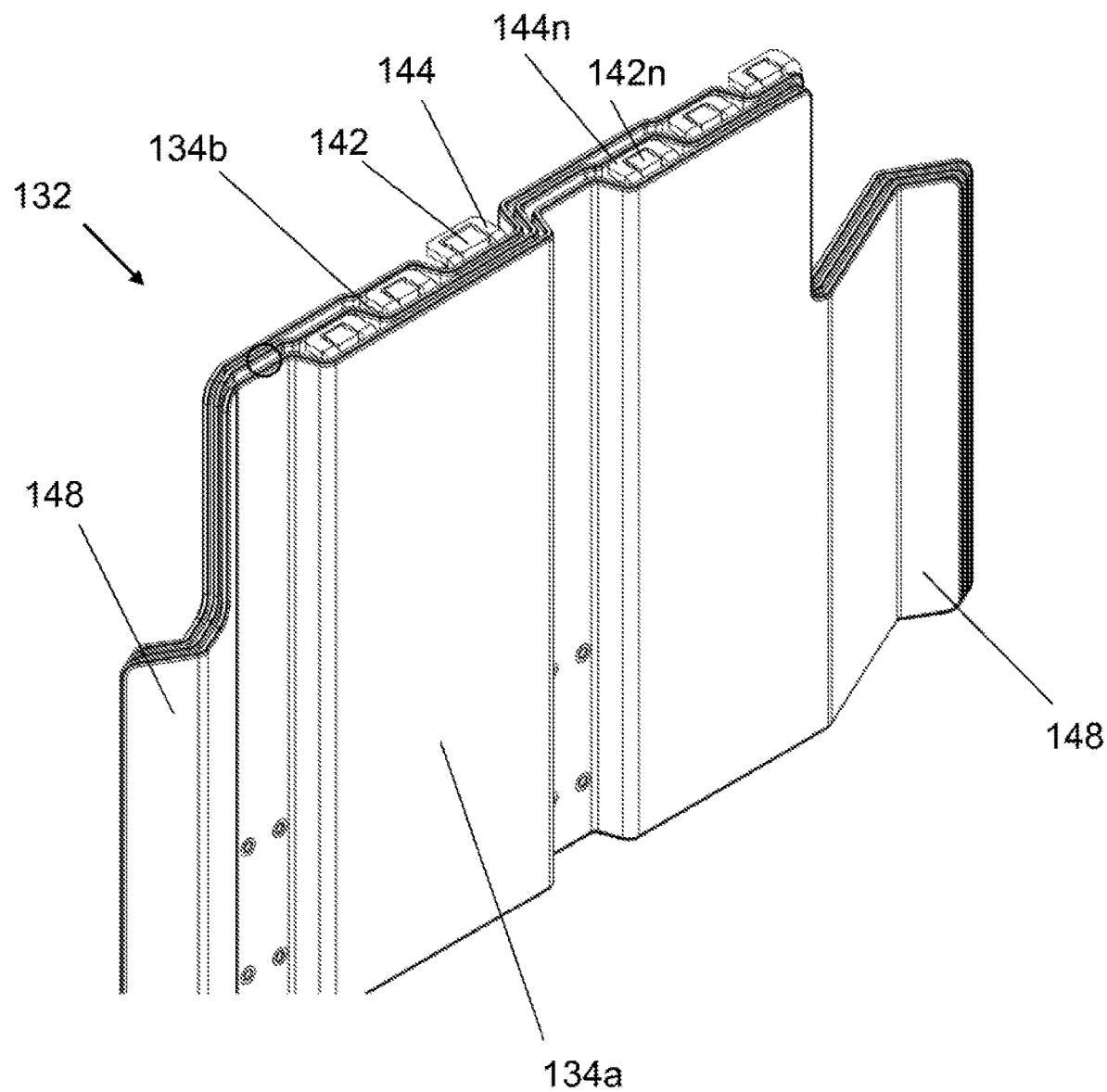

FIG. 6 is a perspective view of FIG. 5, which further emphasizes the compact nesting nature of tiles 134, which is significant for space saving. It is noted that the tiles 134 are illustrated with two rails 142 and two respective corresponding slide elements 144; however, mutatis mutandis, tile positioning mechanism 140 could include a different number of such rails and slide elements, for example one, or three, of more.

Rail 142n is connected to tile 134a and slide element 144n is connected to tile 134b. Thus, an outermost tile 134 (illustrated as tile 134a) of the stack 132 is attached to support base 146 (FIGS. 3 and 4) and the subsequent adjacent inward tile (tile 134b), by way of slide element 144n, slides on rail 142n. It should be understood that the arrangement may be vice versa, mutatis mutandis, wherein the innermost tile 134 is connected to support base 146 and the subsequent adjacent outward tile, by way of its slide element 144, slides on rail 142.

Figure 7:
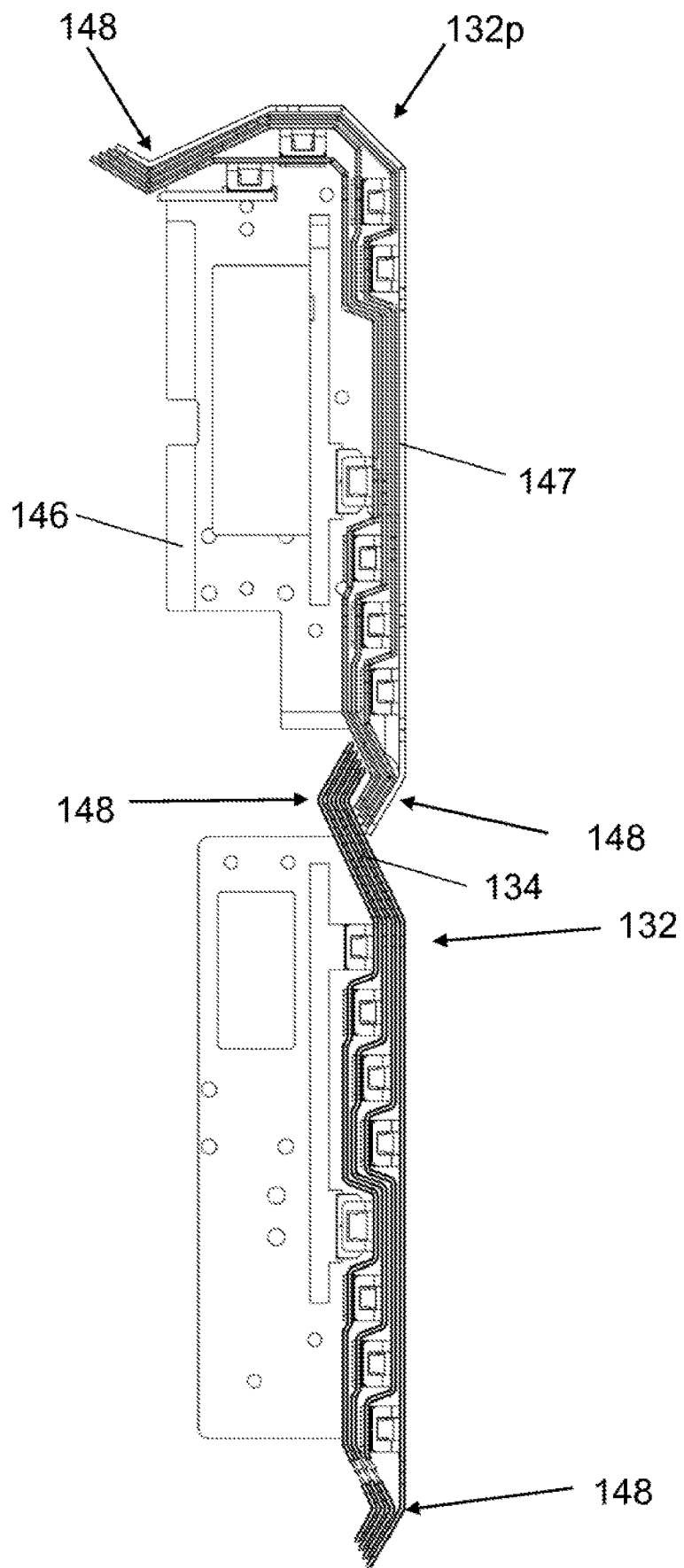

FIG. 7 is a top view of two stacks 132 of four radiation-blocking tiles 134 in a retracted position, illustrating a corner stack 132p. Corner stack 132p is curved or has bends therein to produce an effective corner formation. Side-margins 148 at both sides of corner stack 132p provide for the same tile overlapping as previously described. As such, stacks 132 can form a contiguous radiation protection shield, for example having a generally square profile, although shield structures having other profiles can be produced. Corner stack 132p spans/covers about 90° area located between stacks of two faces of a structure of the assembly of stacks 132. For example, when a radiation shield assembly includes a substantial rectangular or square-like structure, the corner stacks 132p cover the entire 90° area between stacks of adjacent faces.

Figure 8:
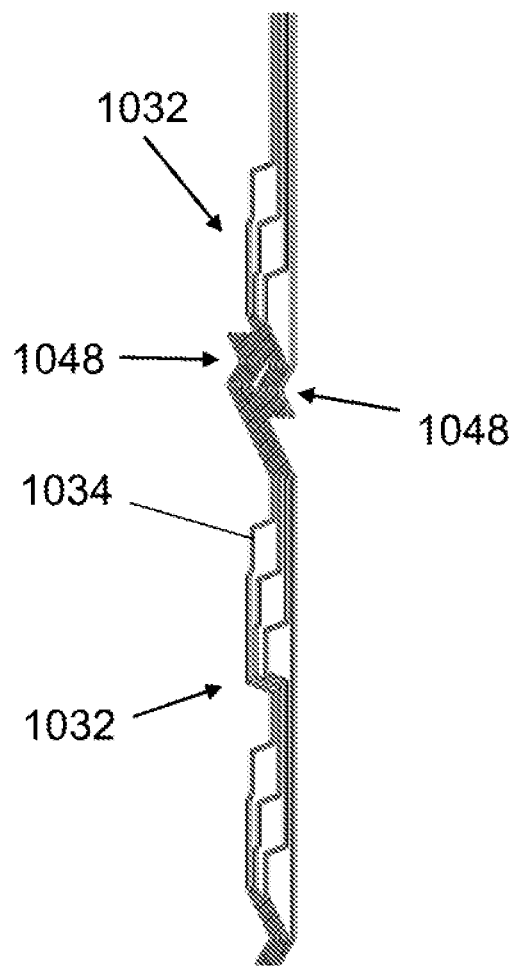

FIG. 8 is a top view of two stacks 1032 of three radiation-blocking tiles 1034 in each stack 1032, in a retracted position, illustrating a zig-zag side margins profile 1048, such that side margins 1048 of neighboring tiles 1034 of neighboring adjacent stacks 1032 at least partially overlap.

Figure 9:
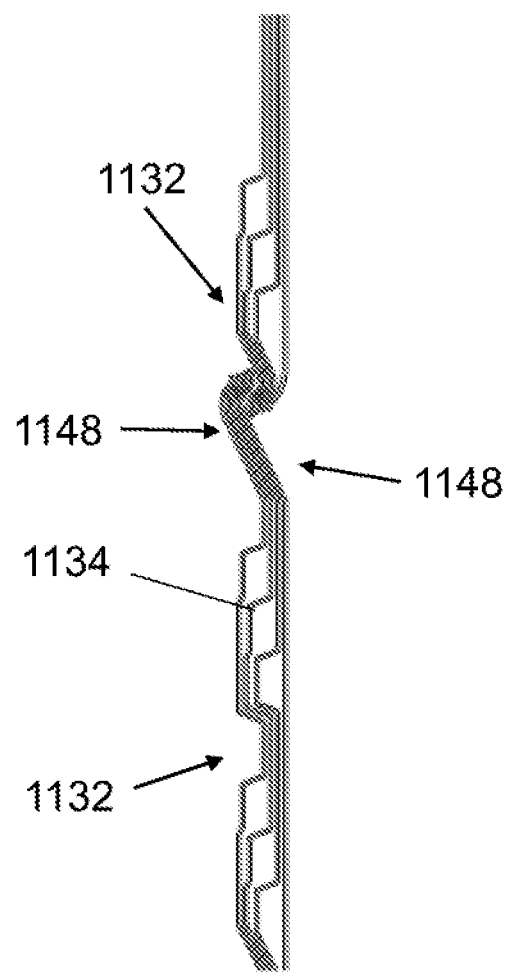

FIG. 9 is a top view of two stacks 1132 of three radiation-blocking tiles 1134 in each stack 1032 in a retracted position, illustrating an S-shaped side margins profile 1148, such that side margins 1148 of neighboring tiles 1134 of neighboring adjacent stacks 1132 at least partially overlap.

As noted above, there is a need to block or minimize, as much as possible, the surroundings from scattered radiation in procedures associated with X-ray-based imaging systems, in order to protect health care providers and technical personnel. To this end the herein-described tiles have the structural features as described above with reference to FIGS. 1-9. These tiles can be manufactured from composite materials as described below with reference to FIGS. 10-20.

The tiles may be manufactured from rigid yet low weight radiation attenuating materials. Suitable materials may include composite materials comprising fabrics (e.g., carbon fibers), a binding material (e.g., epoxy, resin), and one or more radiation attenuating materials (e.g., tungsten). Further suitable materials may include composite materials comprising one or more polymers, and one or more radiation attenuating materials (e.g., tungsten).

Tile structures obtained from such composite materials are useful in a shielding apparatus as herein disclosed with reference to FIGS. 1-9. Nevertheless, the invention further contemplates other structures that may be useful in various additional fields, such as in aerospace where the properties of radiation attenuation, rigidity and low weight are required.

The herein disclosed tiles or other articles may be constructed from a monolayered composite material comprising one or more thermoplastic materials and one or more of radiation blocking materials.

Alternatively, optionally or additionally, tiles or other articles, (e.g., laminate structures) may be constructed from a layered structure including a plurality of layers of fiber (e.g., layers of carbon fiber reinforced polymer; CFRP), and one or more layers of radiation blocking material. For example, the radiation blocking material may be supplied as a powder or as a flexible film. Optionally, a resin is included to immobilize the powder and/or stiffen the structure and/or adhere the layers. The structure may include outer layers of carbon fiber and one or more layers of radiation-blocking material in the middle (a "sandwich" structure). Alternatively, tile structures/other articles may include outer layers of carbon fiber and any combination of one or more layers of radiation-blocking material and carbon fiber in the middle.

Optionally, the carbon fiber is cut to a desired size and/or shape and/or hardened into a final form (e.g., by heating and/or by applying high pressure, and/or by drying at room temperature).

Optionally, the herein disclosed composite materials are formed by injecting a liquid or a pliable raw material of the herein disclosed mixture of a radiation attenuating material and a polymer (e.g., a thermoplastic material) into a mold and solidifying the mixture upon cooling to thereby obtain a rigid structure.

For example, the herein described materials may be used to form radiation shielding tiles of desired sizes and shapes.

Most commonly used radiation-attenuating materials are heavy metals having high density and atomic number. Thus, incorporating those materials in radiation attenuating devices naturally affects the weight of the resultant article.

Structures manufactured from carbon fibers incorporated with the binding polymer or from a thermoplastic material afford rigidity and tensile strength and the radiation attenuating material blocks or minimizes exposure to radiation.

The obtained products/tiles may be further advantageously relatively thin having a thickness of about 0.3 mm or above, and optionally, below.

Various fiber/fabric types are contemplated. For example, the fiber can be a carbon fiber. Alternatively, the fiber may be a glass fiber, an aramid fiber, a boron fiber, or any combination thereof.

The fiber may be in the form of a flexible sheet or a flexible fabric. The thickness of the fiber may vary, for example, the fiber may have a thickness of 0.05 mm or above. For example, 0.1 mm or above, or 0.125 mm or above.

Various thermoplastic materials are contemplated. Non limiting examples include thermoplastic elastomers.

As used herein the terms "radiation protection material", "radiation attenuating material", and their derivatives refer to materials capable of blocking, attenuating, or at least minimizing exposure to radiation. In one or more implementations, the terms include metal or metal alloys. Non limiting examples of radiation attenuating materials include antimony; bismuth; iodine; tungsten; tin; tantalum; erbium; barium; lead; and any combination thereof. Optionally, the radiation attenuating material is provided as a powder. The powder may include particulates having an average size of 0.1 mm or below (e.g., a few microns). Optionally, the radiation attenuating material is mixed with another material such as a polymer, forming a radiation attenuating material-polymer composite (e.g., Tungsten-polymer; Lead-polymer; Bismuth-polymer; Barium-polymer; and any combination of a polymer with a radiation blocking materials).

Optionally, the radiation attenuating material is provided as a thin sheet or as a layer. Optionally, the sheet or layer includes an additional material such as a polymer or a rubber. The sheet or layer may be flexible. The sheet or layer may or may not include additional materials.

The term "binding material" and derivatives thereof as used herein refers to materials that can act as an adhesive and contribute to the rigidity and strength of a structure when combined with the carbon fibers. Optionally, the binding material solidifies upon heating or when pressurized or when dried in open air. Optionally, the binding material has a glue/binding-like property allowing layers to adhere to each other, at least partially. The binding material optionally adheres to the fibers and optionally is at least partially integrated therewith. The binding material may be a polymer, for example a thermoplastic material (e.g., a polyamide). The binding material may be a thermoset resin. By way of example, the thermoset resins may include polyester; epoxy; phenolic; vinyl ester; polyurethane; silicone; polyamide; and polyamide-imide.

In an aspect of the invention there is provided a composition comprising a radiation attenuating material and a binding material. The composition optionally includes a liquid or semi-solid form of the binding material and a radiation attenuating material dispersed therein. The radiation attenuating material may be dispersed, entrapped, and/or distributed within the binding material. Optionally, the radiation attenuating material is dispersed within the binding material as grains having a diameter of 0.1 mm or below.

In an exemplary embodiment, the herein disclosed tile structure or articles are manufactured as a non-layered structure; alternatively, as a multi layered structure. A plurality of layers of carbon cloth or carbon fabric, and/or radiation attenuating material, and/or a binding material may be used. In an exemplary embodiment, the tiles/articles are manufactured from at least two, at least three, at least four, at least five, or at least six layers.

The term "multi-layered" as used herein is interchangeable with the terms "plurality of layers" and "layered" and refers to two or more layers.

In an exemplary embodiment, the herein disclosed tile structure/article is manufactured as a layered, or a multi layered fiber structure. A plurality of carbon fibers may be used. In an exemplary embodiment, the articles are manufactured from at least two, at least three, at least four, at least five, or at least six carbon fiber layers. Optionally, the carbon fibers are one or both external layers. Such configuration may be advantageous as the outer carbon fiber layers provide strength, rigidity and/or structural design for the article.

In one or more embodiments, the binding material is applied onto the carbon fiber layers, allowing adhesive properties and optionally increases strength of the carbon fibers.

Optionally, at least two of the carbon fiber layers are spaced apart by a layer of the radiation attenuating material.

The radiation attenuating material may be disposed within the herein disclosed articles as layers (e.g., sheet). Alternatively, or additionally, the radiation attenuating material may be mixed with the binding material and incorporated or applied to the carbon fibers. Accordingly, the articles or structures are multilayered and include one or more carbon fiber layers onto which a substantially homogenous composition of a binding material and one or more radiation attenuating materials are applied.

Non-limiting examples of a layered or a multilayer structure includes two layers of carbon fiber with an intermediate layer of radiation attenuating material. Yet a further example of a layered or multilayer structure includes four layers of carbon fibers with a middle layer of radiation attenuating material.

Another non-limiting example of a layered or a multilayer structure includes two layers of carbon fiber incorporated with a mixture of a binding material and a radiation attenuating material.

Another non-limiting example of a non-layered structure includes one or more of a thermoelastic material and one or more radiation attenuating materials, optionally in the form of a powder.

FIG. 10 illustrates an exemplary layered carbon fiber composite material/structure 100 having a first and a second carbon fiber layer 101 onto which a substantially homogenous composition 102 is applied. Composition 102 includes a binding material 103 (e.g., an epoxy resin), a first radiation attenuating material 104 and a second radiation attenuating material 105. First radiation attenuating material 104 and second radiation attenuating material 105 may be two different materials or may be the same material presenting different forms (e.g., a powder and a sheet), or may be same material having the same form. First radiation attenuating material 104 and second radiation attenuating material 105 may each be selected from tungsten, lead, bismuth, barium, antimony, and tantalum or other radiation attenuating materials. The composition 102 may be applied on one, two, or all sides of each carbon fiber layer. The resulting product is multi-layered and advantageously low-weight, substantially rigid, and capable of attenuating radiation.

FIG. 11 schematically illustrates a further exemplary structure or composite material 200 having one carbon fiber layer 201 incorporated on both elongated sides thereof a composition 202 that includes a binding material (e.g., an epoxy resin) and one or more radiation attenuating materials.

FIG. 12 schematically illustrates a further exemplary composite material/structure 300 which is similar to composite material 200 but has two carbon fiber layers 301, each surrounded on both elongated sides thereof by a composition 302 having a binding material (e.g., an epoxy resin) and one or more radiation attenuating materials.

FIG. 13 schematically illustrates a further exemplary layered composite material/structure 400. Here, a first radiation attenuating layer 404 and a layer of a second radiation attenuating layer 405 have a sheet-like form and may be optionally a metal foil or a rubber sheet. The radiation attenuating layers 404 and 405 are applied such that two carbon fiber layers 401 surround each of the radiation attenuating layers. Altogether, structure 400 has five layers; three carbon fiber layers 401 and two radiation attenuating layers 404 and 405. Structure 400 is shown to include two different radiation attenuating layers 404 and 405, but a similar structure is herein also contemplated wherein the two radiation attenuating layers are the same. A binding material (such as binding material 103 of FIG. 10) may be applied between each of the layers to facilitate strength and adhesiveness between the layers. Optionally, binding material 103 (not shown) may be applied on all sides of the carbon fiber layers 201, so as to harden or adhere the fibers with the binding material.

FIGS. 14A-14B show another exemplary composite material 500 (FIG. 14B) and a tile 534 (FIG. 14A) manufactured from the composite material. Composite material 500 includes two outer carbon fiber layers 501 on either side of a radiation attenuating material middle layer 502. A binding material, such as resin (not shown) may be provided between the carbon fiber layers to facilitate strength, and adhesion. Optionally, a binding material may be applied on all sides of the carbon fiber layers 501. Optionally, middle layer 502 includes a radiation attenuating material in the form of a metal foil or a flexible sheet (e.g., a radiation attenuating material plus a rubber). The resulting multilayered article can provide radiation attenuation properties at least equivalent to a minimum of 0.1 mm Pb. Tile 534 is assembled from a layered structure as depicted in FIG. 14B. It should be noted that, although tile 534 illustrates a layered structure as shown in FIG. 14B, alternative structures or composite materials as described herein and depicted in the figures are contemplated and applicable with reference to tile 534. Tile 534 can be a rigid non-flat/curved structure used as a shielding element (tile) in a radiation shielding apparatus that blocks radiation emitted from an X-ray imaging system (shown for example in FIG. 2). The one or more recesses 550 of tile 534 are configured to accommodate linear rails 542 and/or other bearing means, or the alike (not shown). The tile 534 is constructed to hold one or more of a sliding mechanism, bearing means, friction rails, sensors and/or attach additional tiles, via a glue, or by screwing, or by other fastening means.

FIG. 15 shows a multilayered composite material/structure 600 including eight carbon fiber sheets or layers 601 and a radiation attenuating material middle layer 602, which may be a metal foil or a flexible rubber sheet or a mixture of radiation attenuating powder and resin. A binding material such as binding material 103 of FIG. 10 may be applied between each of the layers to facilitate strength, and adhesion. Optionally, a binding material may be applied on all sides of the carbon fiber layers 601, to thereby bind the fibers. Optionally, a composition that includes a binding material (e.g., an epoxy resin) and one or more radiation attenuating materials may be applied on one or more of carbon fiber layers 601.

FIG. 16 shows composite material/structure 700 including four carbon fiber layers 701 and in the middle thereof two radiation attenuating layers, i.e., layer 704 having a first radiation attenuating material and layer 705 having a second radiation attenuating material. A binding material such as binding material 103 of FIG. 10 may be applied between each of the layers to facilitate strength, and adhesion. Optionally, a binding material may be applied on all sides of carbon fiber layers 701, to thereby bind the fibers. Optionally, a composition that includes a binding material (e.g., an epoxy resin) and one or more radiation attenuating materials may be applied on one or more of carbon fiber layers 701.

FIG. 17 shows a multi-layered composite material/structure 800 having altogether seven layers. Four carbon fiber layers 801 are disposed such that two layers are spaced apart by a triple middle layer sub-structure formed by two layers of a radiation attenuating material 802 sandwiching a carbon fiber layer 801. A binding material such as binding material 103 of FIG. 10 may be applied between each of the layers to facilitate strength, and adhesion. Optionally, a binding material may be applied on all sides of carbon fiber layers 801, to thereby bind the fibers. Optionally, a composition that includes a binding material (e.g., an epoxy resin) and one or more radiation attenuating materials may be applied on one or more of carbon fiber layers 801.

FIG. 18 shows a multi-layered composite material/structure 900 having altogether seven layers. Four carbon fiber layers 901 are disposed such that two layers are spaced apart by a triple middle layer that includes a layer of a first radiation attenuating material 904, a layer of a second radiation attenuating material 905, and an intermediate non-radiation attenuating spacer layer 906. Spacer layer 906 may be made of a foam (e.g., polyurethane foam) or any other non-radiation attenuating material or non-carbon fiber material. Spacer layer 906 contributes to the strength and stiffness of structure 900. A binding material such as binding material 103 of FIG. 10 may be applied between each of the layers to facilitate strength, and adhesion. Optionally, a binding material may be applied on all sides of the carbon fiber layers 901, to thereby bind the fibers. Optionally, a composition that includes a binding material (e.g., an epoxy resin) and one or more radiation attenuating materials may be applied on one or more of carbon fiber layers 901.

FIGS. 19A-19B show another exemplary composite material 1000 (FIG. 19B) and a tile 1034 (FIG. 19A) manufactured from the composite material. The triple layered composite material 1000 includes two carbon fiber layers 1001 sandwiching a middle of a radiation attenuating material layer 1002. A binding material, such as resin (not shown) may be provided between the layers to facilitate strength, and adhesion. Optionally, a binding material may be applied on all sides of the carbon fiber layers 1001. Optionally, middle layer 1002 includes a radiation attenuating material in the form of a metal foil or a flexible sheet (e.g., a radiation attenuating material plus a rubber). Tile 1034 is a rigid non-flat structure having curves that can be used as a shielding element (tile) in a radiation shielding apparatus that blocks radiation emitted from an X-ray imaging system (shown for example in FIG. 2). One or more recesses 1050 of tile 1034 are configured to accommodate linear rails 1042 and/or other bearing means, or the alike (not shown).

FIGS. 20A-20B illustrates an exemplary single-layered tile structure 1134 (FIG. 20A) manufactured from a composite material/structure 1100 (FIG. 20B) comprising a radiation attenuating material mixed with a polymer (e.g., a thermoplastic elastomer) 1102. The resulting product is single/mono-layer and advantageously low-weight, substantially rigid, and radiopaque. Tile structure 1134 is a non-flat, curved structure which comprises one or more recesses 1150 for accommodating a sliding mechanism, which may include a linear rail 1142. Tile structure 1134 is constructed to hold one or more of a sliding mechanism/bearing means/sensors/attach additional tiles, via a glue or by screwing, or by other mechanical means.

It is to be noted that any of the herein tiles, such as tiles 134 presented in FIGS. 1-7, tiles 1034 presented in FIG. 8 and tiles 1134 presented in FIG. 9 may incorporate any of the herein disclosed materials, such as the composite materials shown in FIGS. 10-20. As illustrated, the tiles of the invention may be produced from a plurality of layers. Alternatively, single layered tiles are contemplated. The tiles may constitute a part of a radiation shielding apparatus (shown for example in FIG. 2), for example an apparatus that can be integrated with or installed onto a C-arm device. As described herein, the tiles require radiation shielding properties, yet should be rigid, light weight and relatively thin.

Optionally, the tiles can be made of any combination of layers including: (a) a plurality of fiber layers (e.g., carbon fiber), incorporated with or bound by a binding material (e.g. resin, epoxy) and one or more layers of radiation attenuating material, in the form of a foil or film (e.g., a foil of a radiation attenuating material, and a flexible film polymer having a radiation attenuating material); (b) a plurality of fiber layers (e.g., carbon fiber), disposed/embedded within and/or bound by a mixture of a binding material (e.g. resin, epoxy) and particles of attenuating material (e.g., in the form of powder); (c) a polymer mixed with a radiation attenuating material.

Optionally, the thickness of the obtained tile product is between about 0.1 mm and about 5 mm. For example, between about 0.5 mm and about 5 mm; between about 1 mm and about 5 mm; between about 1.5 mm and about 5 mm; between about 0.1 mm and about 4 mm; between about 0.1 mm and about 3.5 mm; between about 0.1 mm and about 3 mm; between about 0.1 mm and about 2.5 mm; between about 0.1 mm and about 2 mm; between about 0.1 mm and about 1.5 mm; between about 0.1 mm and about 1 mm, or any thickness in between.

Optionally, the tile has a density of between about 2 g/cc and about 15 g/cc. For example, between about 2 g/cc and about 12 g/cc; between about 2 g/cc and about 10 g/cc; between about 2 g/cc and about 8 g/cc; between about 2 g/cc and about 6 g/cc; between about 2 g/cc and about 4 g/cc; between about 4 g/cc and about 15 g/cc; between about 6 g/cc and about 15 g/cc; between about 8 g/cc and about 15 g/cc; between about 10 g/cc and about 15 g/cc; or any density value in between.

Optionally, the tile is non-flat or curved in a shape that allows relative movement between two or more tiles stacked parallel to each other. In order to achieve dynamic, moving tiles, each tile may include one or more rails/slides/bearings. The one or more rails/slides/bearings may be disposed within one or more recesses (concave portions) in the tiles. For example, each tile may include two rails, each disposed within a dedicated recess. Optionally, each tile includes one rail per 10 cm width (e.g. for a tile having a width of about 32 cm, three rails can be incorporated in respective tile recesses).

Optionally, the tiles can be incorporated with a tile positioning mechanism to allow relative movement of the tiles with respect to each other, forming a longitudinal dynamic radiation attenuating barrier. Various sliding mechanisms are contemplated and applicable. Non-limiting examples of sliding mechanisms include, linear rails, friction rails, sliding mechanisms with linear bearings, sliding mechanisms with rollers, sliding mechanisms with slide-guide strips.

Advantageously, the obtained tiles provide radiation attenuating properties and are rigid allowing stability and stiffness. Further advantageously, the obtained tiles are sufficiently light weight, and thus efficiently dynamic and capable of sliding with respect to each other when provided as an elongated structure, such as a sleeve that can be retracted and deployed to thereby shield a space. A further advantageous property is associated with the tile structure, which is minimalistic in thickness, while still presenting rigidity sufficient to achieve long term stability, resistance to external forces and to allow efficient sliding properties.

Yet another aspect of the invention pertains to a method of producing a rigid low-weight radiation attenuating structure, the method comprising: providing one or more carbon fiber fabrics; applying onto and/or between the one or more layers a binding material; and applying or providing onto and/or between the one or more layers a radiation attenuating material.

In one or more embodiments, the method comprises a step of curing the carbon fibers, thereby producing a rigid radiation attenuating structure.

In one or more embodiments, the method comprises a step of mixing the binding material and the radiation attenuating material to produce a liquid or semi-solid substantially homogenous mixture comprising particulates of the radiation attenuating material and the binding material.

In one or more embodiments, the method further comprises applying a layer of the mixture onto the one or more layer of carbon fiber.

In one or more embodiments, the radiation attenuating material is in a foil or film-like form. In one or more embodiments, the radiation attenuating material is in a powder form.

In view of the above, an aspect of the present invention pertains to a radiation attenuating composite material in accordance with the disclosure herein above.

Another aspect of the invention pertains to a substantially homogenous radiation attenuating composition in accordance with the disclosure herein above.

Yet another aspect of the invention pertains to a rigid tile structure having a composite material in accordance with the disclosure herein above.

Yet another aspect of the invention pertains to a rigid non-flat structure having a composite material in accordance with the disclosure herein above.

Yet another aspect of the invention pertains to medical radiation shielding apparatus including a rigid tile structure in accordance with the disclosure herein above.

Each of the following terms: 'includes', 'including', 'has', 'having', 'comprises', and 'comprising', and their linguistic equivalents, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

The term 'consisting essentially of' as used herein means that the scope of the claim is limited to the specified elements and those that do not materially affect the basic and novel characteristic(s) of the claimed device and materials.

Each of the phrases 'consisting of' and 'consists of', as used herein, means 'including and limited to'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and thus, the two equivalently meaning phrases may be used interchangeably.

The term 'about', is some embodiments, refers to ±30% of the stated numerical value. In further embodiments, the term refers to ±20% of the stated numerical value. In yet further embodiments, the term refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the broad scope of the appended claims.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for positioning tiles in a radiation shielding apparatus comprising a plurality of stacks of positionable radiation-shielding tiles arranged in a contiguous peripheral configuration, said method comprising:
    extending and retracting the tiles in each stack along a vertical axis between (a) a retracted position and (b) a vertically extended position;
    wherein in both the retracted position and the vertically extended position, the tiles of each of the plurality of radiation shielding stacks at least partially overlap tiles of subsequent and adjacent tile stack at corresponding opposing and adjacent side-margins thereof; and
    wherein the tiles in each stack have opposed faces with a rail extending in a vertical direction attached to one of the opposed faces and a slide element extending in a vertical direction attached to another of the opposed faces to allow each tile to slide along a length of each adjacent tile within a stack.

2. The method of claim 1, wherein the tiles, as well as their corresponding opposing side-margins, are non-flat.

3. The method of claim 1, wherein the non-flat corresponding opposing side-margins have a zig-zag or V-shaped profile.

4. The method of claim 2, wherein the non-flat corresponding opposing side-margins have a wavy or S-shaped profile.

5. The method of claim 1, wherein the stacks of tiles form a structure having two or more faces, each face including at least one tile stack; and corner tile stacks connecting two adjacent faces thereof.

6. The method of claim 1, wherein corner tile stacks cover an area of at least about a 90.degree. angle between two adjacent faces.

7. The method of claim 1, wherein the rails and slide elements on vertically adjacent pairs of tiles are peripherally spaced apart so that they do not overlap when the tiles are retracted in a stack to reduce thickness.

8. The method of claim 7, wherein the rails and slide elements within a stack are nested in recesses formed the opposed faces of the tiles, thereby providing a compact structure of tiles in a stack.

9. The method of claim 8, wherein the recesses accommodate therein a rail of said tile and a respective slide element of a sequentially adjacent tile.

10. The method of claim 9, wherein the recesses of vertically adjacent tiles within each stack are aligned such that the recesses in vertically adjacent tiles nest when the stack is retracted, thereby providing for a compact structure of tiles in a stack.

11. The method of claim 1, wherein each tile comprises a first side margin with a concave or V-shaped profile and an opposite second side margin with a convex or upside down V-shaped profile, and the tiles of subsequent and adjacent tile stacks are arranged such that the concave or V-shaped profile of the tiles within one stack overlap the convex or upside down V-shaped profile of the tiles within the subsequent and adjacent tile stack.

12. The method of claim 1, wherein the tiles are manufactured from a composite material comprising at least one carbon fiber layer, a binding material and at least one radiation attenuating material.

13. The method of claim 12, wherein the binding material comprises a thermoset resin, a polyester, a vinyl ester, a polyamide, or a combination thereof.

14. The method of claim 13, wherein the thermoset resin comprises an epoxy resin.

15. The method of claim 12, wherein the radiation attenuating material comprises a metal selected from the group consisting of: tungsten; lead; bismuth; antimony; barium; and tantalum, or a combination thereof.

16. The method of claim 12, wherein the composite material further comprises a material selected from the group consisting of: aramid; aluminum; ultra-high-molecular-weight polyethylene; and glass fibers, and a combination thereof.

17. The method of claim 12, wherein the composite material comprises a plurality of carbon fiber layers; and a mixture of a binding material and particles of radiation attenuating material.

18. The method of claim 12, wherein the radiation attenuating material includes a foil or a film-like structure.

19. The method of claim 12, wherein the radiation attenuating material includes a powder mixed within said binding material, and wherein said mixture is applied onto at least one of said fibers.

20. The method of claim 1, wherein the tiles are manufactured from a thermoplastic material mixed with a radiation attenuating material.

* * * * *